(12) United States Patent
Stefansson et al.

(10) Patent No.: US 10,245,171 B2
(45) Date of Patent: Apr. 2, 2019

(54) HAND SUPPORT AND METHOD FOR USING THE SAME

(71) Applicant: Ossur Iceland ehf, Reykjavik (IS)

(72) Inventors: Stefan Orn Stefansson, Reykjavik (IS); Dana Stewart Marlin, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 280 days.

(21) Appl. No.: 15/095,448

(22) Filed: Apr. 11, 2016

(65) Prior Publication Data

US 2016/0296359 A1 Oct. 13, 2016

Related U.S. Application Data

(60) Provisional application No. 62/286,511, filed on Jan. 25, 2016, provisional application No. 62/145,008, filed on Apr. 9, 2015, provisional application No. 62/144,993, filed on Apr. 9, 2015.

(51) Int. Cl.
| | |
|---|---|
| *A61F 5/01* | (2006.01) |
| *A61F 5/058* | (2006.01) |
| *A61F 5/10* | (2006.01) |
| *A61F 5/048* | (2006.01) |

(52) U.S. Cl.
CPC ............ *A61F 5/0118* (2013.01); *A61F 5/048* (2013.01); *A61F 5/05866* (2013.01); *A61F 5/05875* (2013.01); *A61F 5/10* (2013.01)

(58) Field of Classification Search
CPC .... A61F 5/0118; A61F 5/048; A61F 5/05866; A61F 5/05875; A61F 5/10; A61F 13/107; A61F 5/013; A63B 23/16
See application file for complete search history.

(56) References Cited

U.S. PATENT DOCUMENTS

| | | | |
|---|---|---|---|
| 1,471,948 A | 10/1923 | Cox et al. | |
| 1,568,668 A | 1/1926 | Harrison | |
| 2,388,330 A | 11/1945 | Jungmann | |
| 2,477,126 A | 7/1949 | Hartmann | |

(Continued)

FOREIGN PATENT DOCUMENTS

| | | |
|---|---|---|
| EP | 0217451 A1 | 4/1987 |
| EP | 1138288 A1 | 10/2001 |

(Continued)

OTHER PUBLICATIONS

Colditz et al. "A New Splint Design for the Thumb CMC Joint", Nea International bv, www.push.eu, 2010, pp. 1-11.

(Continued)

*Primary Examiner* — Ophelia A Hawthorne

(74) *Attorney, Agent, or Firm* — Workman Nydegger

(57) ABSTRACT

A hand support including a base component arranged for securing to at least a portion of a hand, an anchor element adjustably connected to the base component and arranged for grasping a thumb, and a counterforce device connecting to the base component and the anchor element. The counterforce device arranged to generate a counterforce in combination with or against the base component and anchor element. The hand support may be arranged to provide traction for an extended period to remedy complications of the hand and associated joints.

16 Claims, 25 Drawing Sheets

(56) References Cited

U.S. PATENT DOCUMENTS

| | | | |
|---|---|---|---|
| 2,523,606 A | 11/1950 | Young | |
| 2,646,794 A | 7/1953 | Baer | |
| 3,769,970 A * | 11/1973 | Swanson | A61F 5/0118 |
| | | | 602/11 |
| 3,815,908 A | 6/1974 | Hashimoto | |
| 4,382,439 A | 5/1983 | Shen | |
| 4,653,490 A | 3/1987 | Eisenberg | |
| 4,658,441 A | 4/1987 | Smith | |
| 4,665,907 A | 5/1987 | Leverette | |
| 4,702,234 A | 10/1987 | Huntjens | |
| D300,948 S | 5/1989 | Harris et al. | |
| 4,862,877 A * | 9/1989 | Barber | A61F 5/05866 |
| | | | 602/22 |
| 4,953,568 A | 9/1990 | Theisler | |
| 5,279,545 A | 1/1994 | Reese, Sr. | |
| 5,324,251 A * | 6/1994 | Watson | A61F 5/05866 |
| | | | 602/16 |
| D360,467 S | 7/1995 | Sydor et al. | |
| 5,787,896 A | 8/1998 | Sackett | |
| D405,180 S | 2/1999 | Reina | |
| 5,899,870 A | 5/1999 | Deirmendjian et al. | |
| 6,146,348 A | 11/2000 | Slautterback | |
| 6,165,148 A | 12/2000 | Carr-Stock | |
| 6,196,985 B1 | 3/2001 | Slautterback | |
| 6,219,843 B1 | 4/2001 | Passi et al. | |
| 6,261,252 B1 | 6/2001 | Darcey | |
| 6,325,772 B1 | 12/2001 | Scheuermann et al. | |
| 6,371,932 B1 | 4/2002 | Foote | |
| D461,901 S | 8/2002 | Rodgers | |
| 6,475,174 B1 | 11/2002 | Chow | |
| 6,491,694 B1 | 12/2002 | Orsak | |
| 6,496,984 B1 | 12/2002 | Chow | |
| 6,520,925 B1 | 2/2003 | Thibodo, Jr. | |
| D473,653 S | 4/2003 | Weaver, II et al. | |
| 6,569,111 B2 | 5/2003 | Herzberg | |
| 6,702,772 B1 | 3/2004 | Colditz | |
| 6,783,507 B1 | 8/2004 | Fisher | |
| 7,033,331 B1 | 4/2006 | Hely | |
| 7,056,298 B1 | 6/2006 | Weber | |
| D528,263 S | 9/2006 | Van Trojen | |
| D558,883 S | 1/2008 | Ortiz | |
| D584,822 S | 1/2009 | Weber | |
| 7,713,223 B2 | 5/2010 | Weber et al. | |
| D620,058 S | 7/2010 | Gaedke | |
| 7,824,352 B2 | 11/2010 | Jaccard | |
| 7,854,714 B1 | 12/2010 | Weber et al. | |
| 7,914,475 B2 | 3/2011 | Wyatt et al. | |
| D643,931 S | 8/2011 | Voskuilen | |
| 8,114,041 B2 | 2/2012 | Wyatt et al. | |
| 8,657,771 B2 | 2/2014 | Weaver, II et al. | |
| 8,784,348 B2 | 7/2014 | Farrell et al. | |
| 2001/0041855 A1 | 11/2001 | Voskuilen | |
| 2002/0002348 A1 | 1/2002 | Wiggins et al. | |
| 2002/0169403 A1 | 11/2002 | Voskuilen | |
| 2005/0273027 A1 * | 12/2005 | Farrell | A63B 23/16 |
| | | | 602/21 |
| 2006/0264792 A1 | 11/2006 | Bonn | |
| 2008/0262400 A1 | 10/2008 | Clark et al. | |
| 2009/0131843 A1 | 5/2009 | Weber et al. | |
| 2009/0240182 A1 | 9/2009 | Weber et al. | |
| 2013/0041301 A1 | 2/2013 | Grim et al. | |
| 2013/0197411 A1 | 8/2013 | Bolla | |
| 2013/0253400 A1 | 9/2013 | Massa | |
| 2015/0142131 A1 | 5/2015 | Egilsson et al. | |

FOREIGN PATENT DOCUMENTS

| | | |
|---|---|---|
| GB | 2094152 A | 9/1982 |
| WO | 9627349 A1 | 9/1996 |
| WO | 9829060 A1 | 7/1998 |
| WO | 2007066367 A2 | 6/2007 |
| WO | 2007145504 A1 | 12/2007 |
| WO | 2014148906 A1 | 9/2014 |
| WO | 2015170973 A1 | 11/2015 |

OTHER PUBLICATIONS

"Bend, A Revolutionary Medical Finger Split", Behance, https://www.behance.net/gallery/16265171/bend-a-revolutionary-medical-finger-splint-, retrieved from the Internet on Apr. 8, 2016, pp. 1-19.

"Bort Sellafix Thumb Orthoses", The New Range: Made of Thermoplastic Material in a Unique Perforated Design, Bort Medical, www.bort.de, retrieved from the Internet on Apr. 8, 2016, 2 pages.

"Thumb Injuries Management Solutions for Acute and Chronic Disorders", BSN Medical Inc., www.bsnmedical.com, 2016, pp. 1-4.

"CMC Controller", Weber Orthopedic Inc., DBA Hely & Weber, 2008, 2 pages.

Product Information, "Ortho Push Braces", www.push.eu, retrieved from the Internet on Apr. 4, 2016, 2 pages.

"The Solutions for the Hand, The Hand Orthoses Program of Bort Made of Thermoplastic Material", Bort Medical, www.bort.de, retrieved from the Internet on Apr. 8, 2016, 4 pages.

International Search Report from corresponding PCT Application No. PCT/US2016/026912, dated Aug. 2, 2016.

* cited by examiner

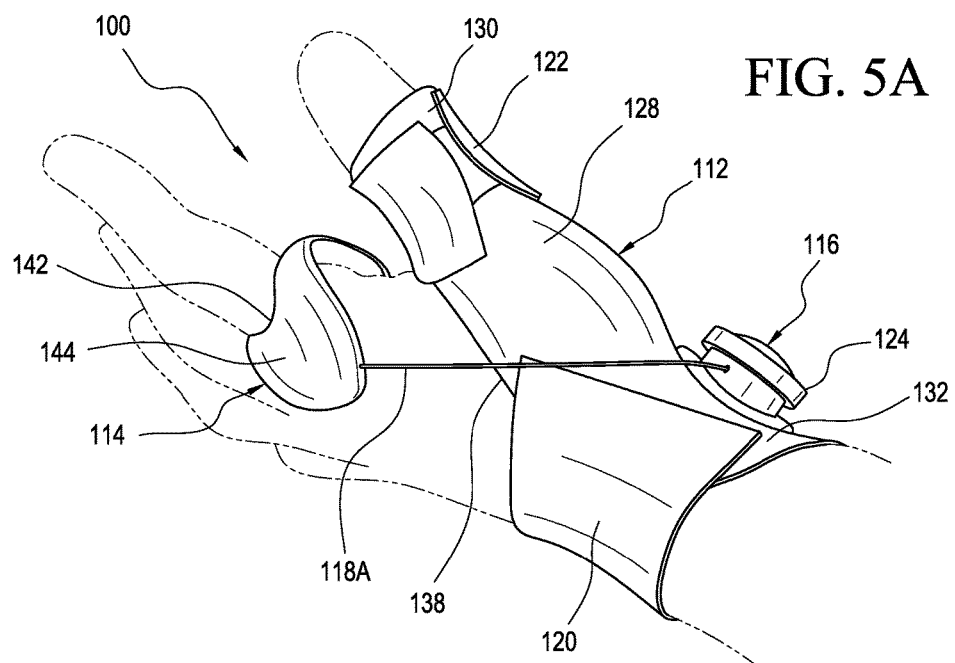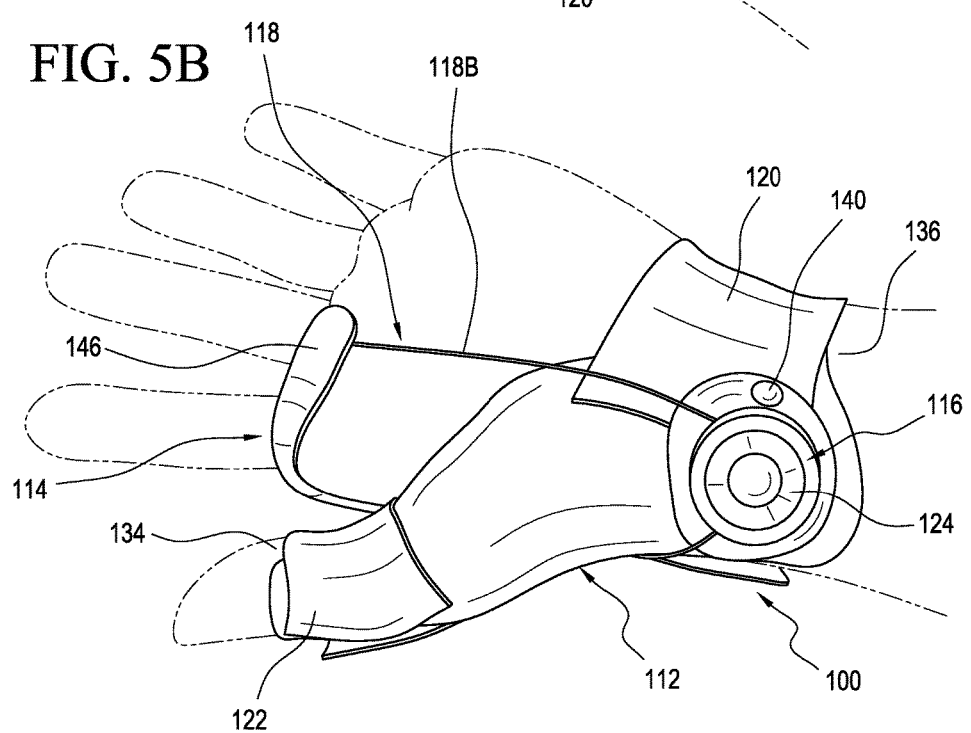

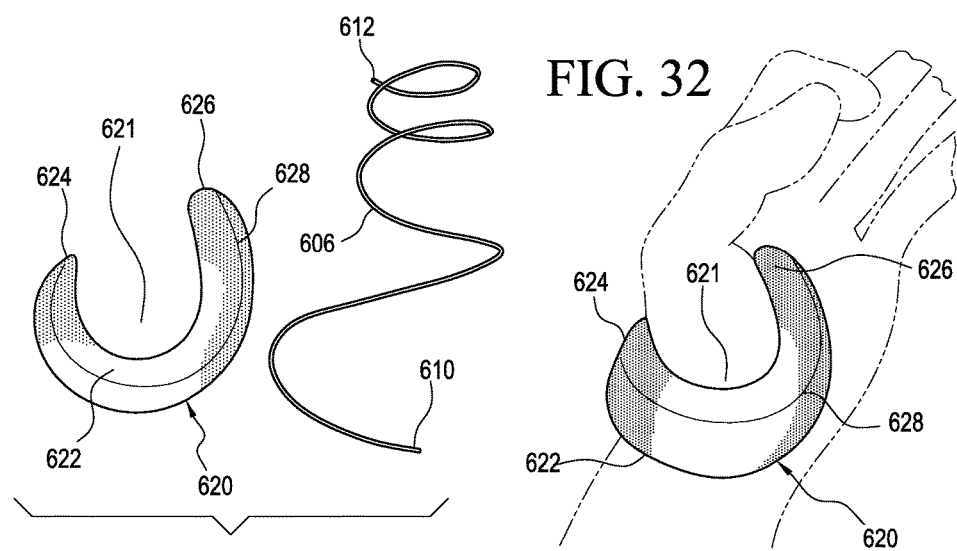
FIG. 31
FIG. 32
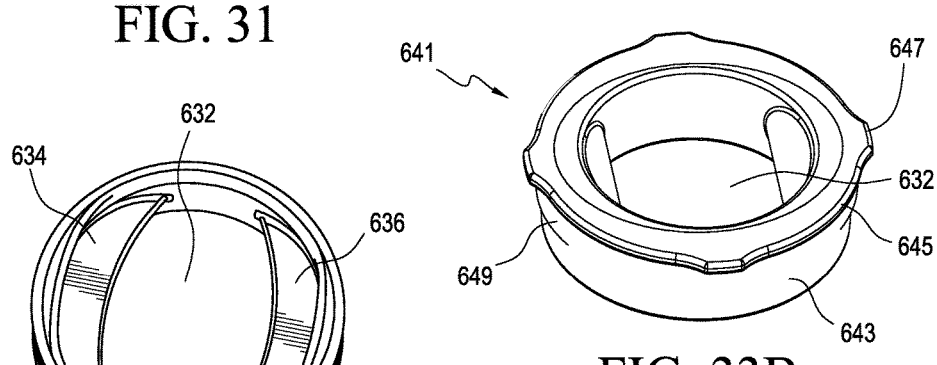
FIG. 33A
FIG. 33B
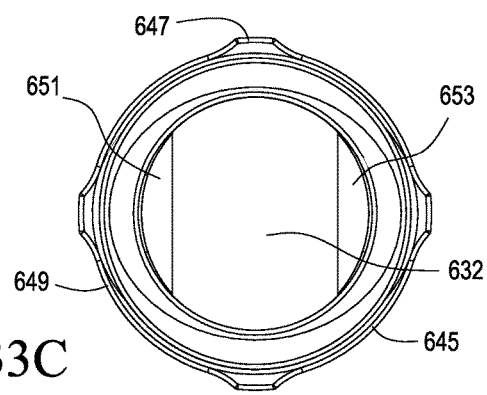
FIG. 33C

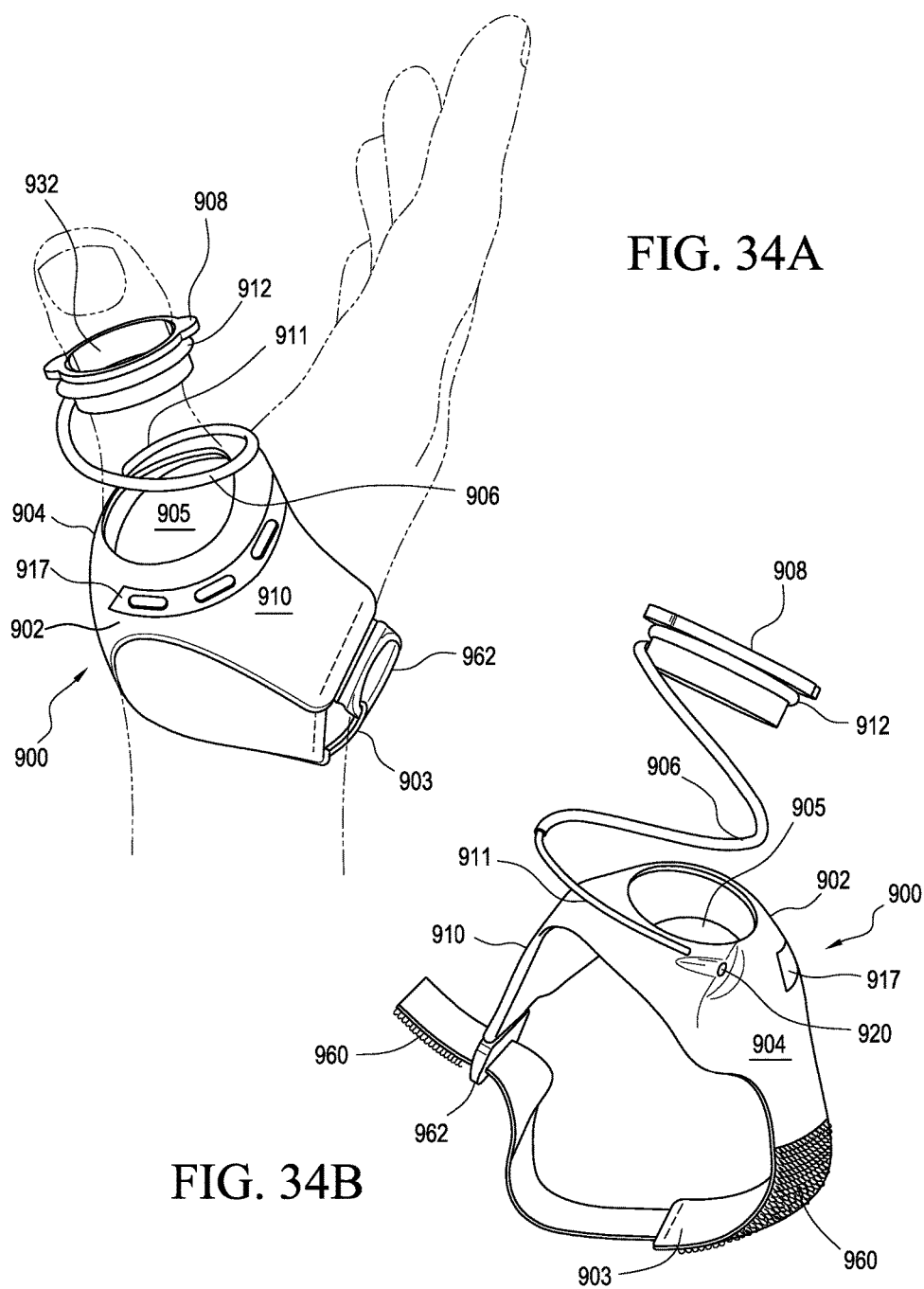

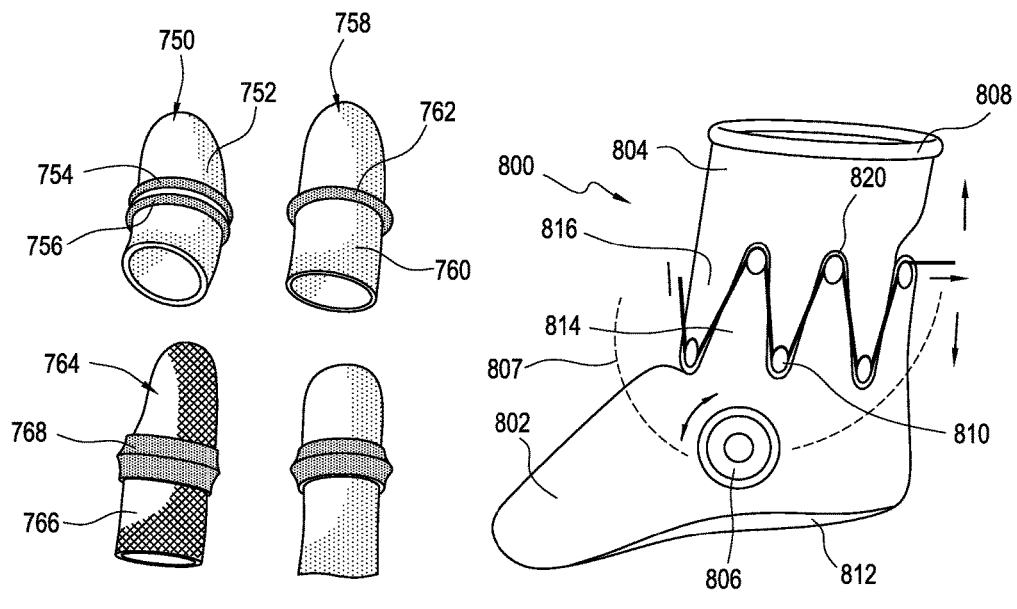
FIG. 44
FIG. 45
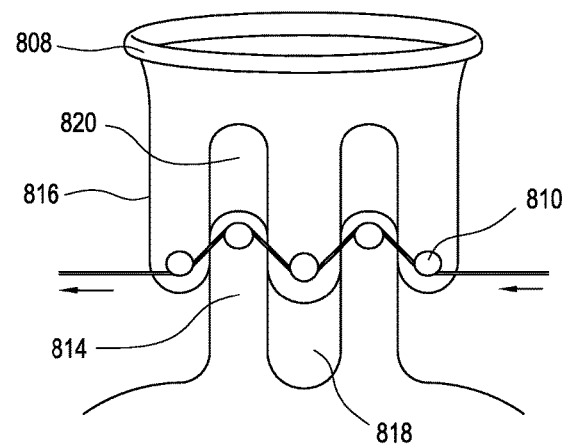
FIG. 46

HAND SUPPORT AND METHOD FOR USING THE SAME

FIELD OF THE DISCLOSURE

The disclosure relates to orthopedic devices and particularly to hand supports for treating various hand complications. The hand support may be arranged to employ traction for an extended period to remedy complications of the hand and associated joints.

BACKGROUND

In orthopedic medicine, traction refers to various mechanisms for straightening or aligning bones in a desired manner. An approach to knee osteoarthritis (OA) management involves invasive joint distraction. Experience with invasive joint distraction indicates that distracting the OA afflicted joint for an extended period may halt or reverse the disease.

Initially, joint distraction was used in the treatment of joint malalignment and joint contracture. An external fixation frame was used to actively reposition the joint and to increase the range of motion. Distraction was performed to prevent damage (compression) of the joint cartilage during the forced repositioning. In some of these patients OA was present in the treated joint and an unexpected clinical improvement of the OA was observed. These clinical observations led to a proof-of-concept study examining the benefit of joint distraction, by treating young patients with severe ankle OA. Two-thirds of patients treated for 3 months with joint distraction experienced significant clinical benefits for a period of up to 10 years. Based on preliminary radiographic outcomes in a few patients, joint distraction may lead to tissue structure modification.

Osteoarthritis can be found in other joints and there is reason to believe that distraction will have the same effect in other joints as described for the knee above. One major joint for OA is the first CMC joint (first carpal-metacarpal joint, also known as the trapeziometacarpal joint or the basal thumb joint) and OA of this joint is commonly considered thumb arthritis.

As shown in FIGS. 1 and 2, the CMC joint is where the metacarpal bone of the thumb meets the trapezium bone at the wrist. The trapezium forms a recess into which the metacarpal bone rests, and both bones are covered with cartilage. Thumb arthritis results in severe hand pain, swelling, decreased strength and range of motion, and makes routine tasks painful and difficult to achieve. Thumb arthritis is one of the most common forms of OA due in part to the significant forces the CMC joint undergoes in routine activities.

Thumb arthritis occurs when the cartilage breaks down and wears away from adjoining ends of the metacarpal and trapezium bones at the first CMC joint. In early stages of thumb arthritis, there may be inflammation about the joint and isolated breakdown of cartilage around one or a few areas of the cartilage surface. As the arthritis progresses, bone spurs may develop and the thumb may contract into the palm, with pain and mobility of the hand worsening.

Treatment of arthritis in the early stages may involve joint protection, such as through hand supports arranged to reduce thumb movement or completely immobilize the thumb. Known hand supports may be soft or hard varieties, with soft hand supports providing better freedom of movement but less immobilization, whereas hard hand supports provide superior immobilization but better pain relief. Other options for treatment of hand arthritis include conservative treatments such as joint protection, physical therapy, massage, and cold and hot therapy. For moderate to severe hand arthritis, treatment options include medicines, injections, and invasive surgical treatment including ligament reconstruction, joint replacement, and joint fusion.

Medicines may cause side effects and diminishing returns over time, merely masking the pain but failing to treat the cause of the arthritis. Injections are effective however they may lead to a weakening of the joint and result in further breakdown of cartilage since they, like medicine, do not treat the source of the arthritis. The surgical treatments, while effective in treating the source of the arthritis, are invasive and recovery from surgical treatment for a return to normal activities is time-consuming.

The CMC joint may become inflamed due to excessive motion of the joint. While immobilization of the joint can reduce pain and inflammation, it does not allow for the functional use of the joint. A dynamic stability split may be used to reduce excessive motion of the joint while serving to provide traction to the joint to treat osteoarthritis.

Therefore, there is a desire for a solution to treat moderate to severe hand arthritis in a non-invasive manner that concentrates on the source of the arthritis rather than just the pain.

SUMMARY

Noninvasively treating hand arthritis may be achieved by creating traction of the thumb joints and applying a force on the thumb or hand in opposition to an anchor located at a position on the hand or wrist. Adjustment means may be provided to enable incremental adjustment of the force according to a treatment protocol adapted for an individual suffering from arthritis.

Embodiments of hand supports and methods for using the same are described and are intended to function by creating traction to treat thumb arthritis. Embodiments are also provided for a versatile hand support for treating earlier complications of thumb arthritis and other complications of the hand.

Embodiments described herein generally relate to a hand support having a base component for securing to at least a portion of a hand. The base component can be supplemented with rigid, non-rigid, flexible or resilient features, such as a joint stabilizer for reinforcing a hand. The hand support generally includes an anchor element adjustably connected to the base component for grasping a thumb. The hand support also generally includes a counterforce device connecting to the base component and the anchor element. The counterforce device is arranged to generate a counterforce in combination with or against the base component and the anchor element. The embodiments are employed for providing traction by straightening or aligning bones in a desired manner, particularly by distraction or applying a counterforce to pull a CMC joint apart while the hand support is anchored on the hand or wrist.

BRIEF DESCRIPTION OF THE DRAWINGS

These and other features, aspects, and advantages of the present disclosure will become better understood regarding the following description, appended claims, and accompanying drawings.

FIG. 5A is a perspective view of another embodiment of a hand support generally showing a dorsal aspect of the hand.

FIG. 5B is a perspective view of the hand support of FIG. 5A generally showing a palmar aspect of the hand.

FIG. 31 is a schematic view of the elastic element and a variation of the base component of the thumb support of FIG. 29A.

FIG. 32 is a perspective view of the base component of FIG. 31 on a hand of a wearer.

FIG. 33A is a variation of the retainer in the thumb support of FIG. 29A.

FIG. 33B is a perspective view of another variation of a retainer.

FIG. 33C is a plan view of the retainer of FIG. 33B.

FIG. 34A is a perspective view of another thumb traction device.

FIG. 34B is a perspective schematic view of the thumb traction device of FIG. 34A with the elastic element detached.

FIG. 44 includes schematic views of various seal elements for use with the thumb traction device of FIG. 43.

FIG. 45 is a perspective view of another thumb traction device in a contracted configuration.

FIG. 46 is a perspective view of another thumb traction device in an extended configuration.

Figure 1:
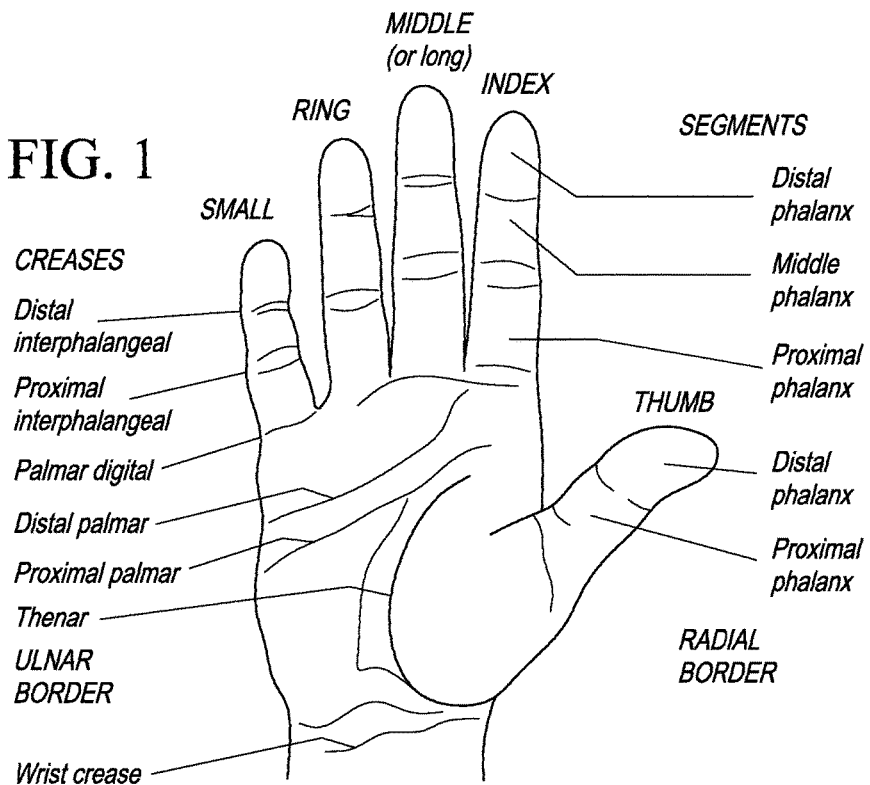
FIG. 1 is a schematic view of a hand anatomy.
Figure 2:
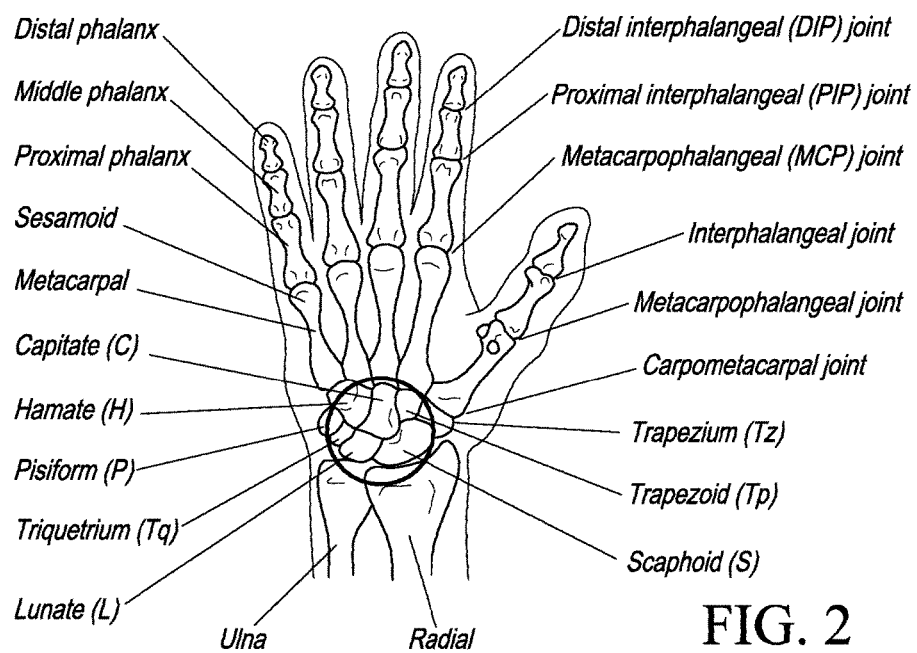
FIG. 2 is a schematic view of a hand skeletal anatomy.

The drawing figures are not drawn to scale, but instead are drawn to provide a better understanding of the components, and are not intended to be limiting in scope, but rather to provide exemplary illustrations.

DETAILED DESCRIPTION OF VARIOUS EMBODIMENTS

A. Overview

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the embodiments disclosed, but on the contrary, the intention covers all modifications, alternative constructions, combinations, and equivalents falling within the spirit and scope of the disclosure.

It will be understood that, unless a term is defined in this disclosure to possess a described meaning, there is no intent to limit the meaning of such term, either expressly or indirectly, beyond its plain or ordinary meaning.

B. Hand Support Embodiments

The embodiments of the hand support are generally arranged to grab a digit of the hand, such as a thumb or finger, or portion of the hand, and pull and maintain a joint apart, such as the CMC joint. A distraction or counterforce is used to pull the joint apart while the hand support is anchored on the hand or wrist. The terms "hand support" and "thumb support" may be used interchangeably in the following discussion. Various means may be used to incrementally adjust the distraction force over a period of treatment. Additionally, or alternately, the hand support may provide dynamic stability which may focus on preventing excessive motion of a joint while also providing a force on the joint that may vary according to movement.

Figure 3:
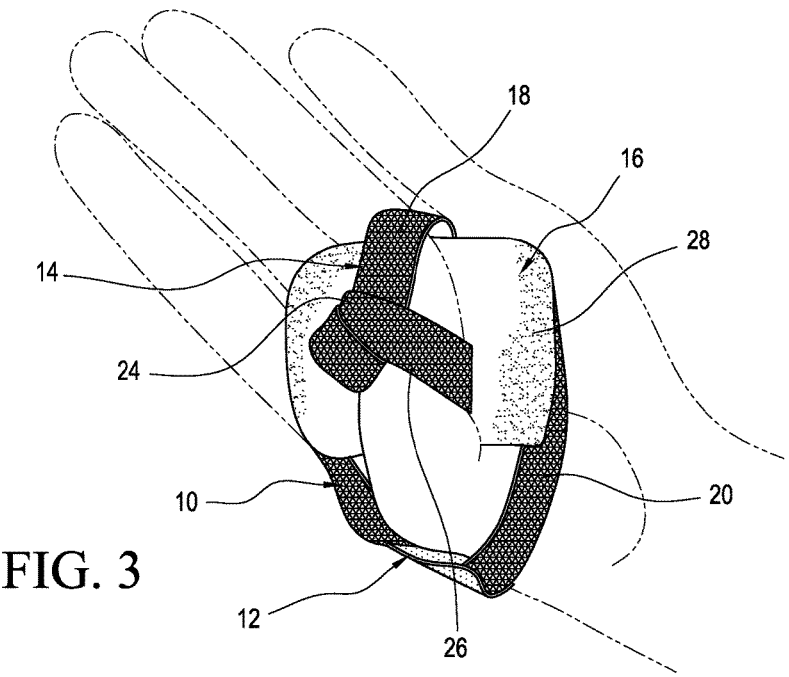
FIG. 3 is a perspective view of an embodiment of a hand support generally showing a palmar aspect of the hand.
Figure 4:
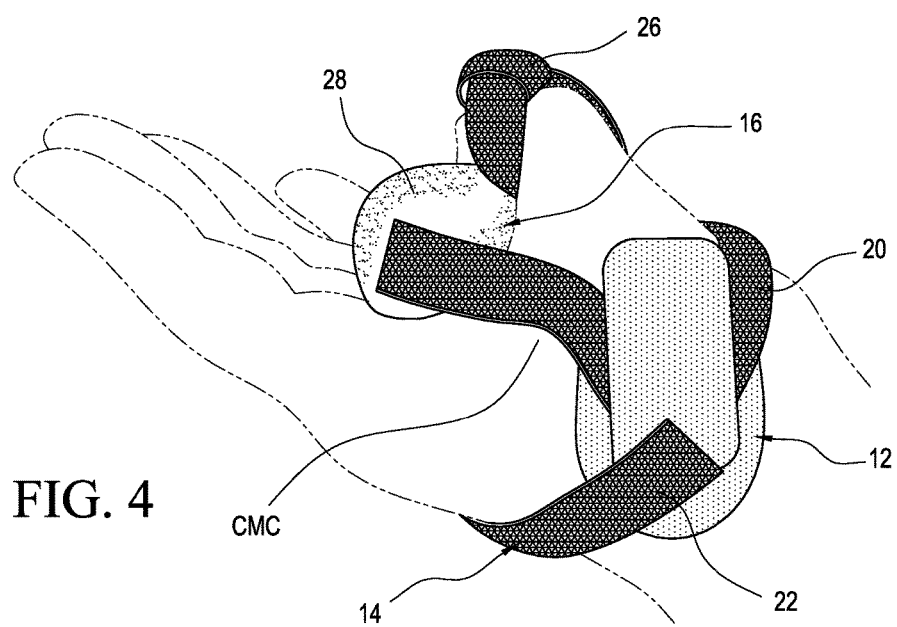
FIG. 4 is a perspective view of the embodiment of FIG. 3 showing a partial dorsal aspect of the hand.

In the embodiment of FIGS. 3 and 4, a base component 12 is arranged for securing to at least a portion of a hand. The base component 12 extends about the wrist or about the hand. An anchor element 14 adjustably connects to the base component 12 and is arranged for grabbing a thumb. A counterforce device 16 connects to the base component 12 and the anchor element 14. The counterforce device 16 is arranged to generate a counterforce in combination with or against the base component 12 and/or anchor element 14.

The anchor element 14 may comprise a strap 18 having a first end 22 securing to the base component 12 and a second end 24 arranged to secure to a thumb. The second end 24 of the strap 18 defines a grip 26 arranged to hold onto a thumb.

The counterforce device 16 may comprise a bolster 28 connected to the base component 12 and arranged to be received by a palm and leveraged over a first carpal-metacarpal joint to translate into traction in the thumb. The bolster 28 tethers to the base component 12 by a second strap 20. The bolster 28 may be compressible or rigid.

Referring to the hand support 100 embodiment of FIGS. 5A and 5B, the base component 112 includes a rigid or substantially rigid shell 128 having a thumb portion 130 arranged to encircle the thumb. The wrist portion 132 is arranged to extend about at least a portion of the wrist. Thumb portion 130 defines a split 134 and a thumb strap 122 encircles the thumb portion 130 to reduce the split upon tensioning of the thumb strap 122. The thumb portion 130 extends continuously to the wrist portion 132.

The wrist portion 132 defines a clearance 136 and a wrist strap 120 extends from opposed first and second sides 138, 140 of the wrist portion 132 to tension over the wrist and maintain the wrist portion 132 on the wrist. The wrist strap 120 releasably and adjustably secures to the first side 138 and pivotally attaches to the second side 140.

The counterforce device 116 includes a tensioning device 124 connected to an elongate element 118 securing to the anchor element 114, and secured to the base component 112. The dial tensioning element 124 secures to a wrist portion 132 of the base component 112. The tensioning device 124 is arranged to incrementally tension the elongate element 118 and draw the anchor element 114 toward the base component 112. The elongate element 118 includes first and second portions 118A, 118B extending over dorsal and palmar portions of the hand and securing to the anchor element 114.

The anchor element 114 has an opening 142 arranged to extend over a finger and retain therewith. The anchor element 114 is arranged to extend between an index finger and the thumb. The anchor element 114 defines first and second sections 144, 146 compliantly extending over dorsal and palmar aspects of the hand.

Figures 6A, 6B:
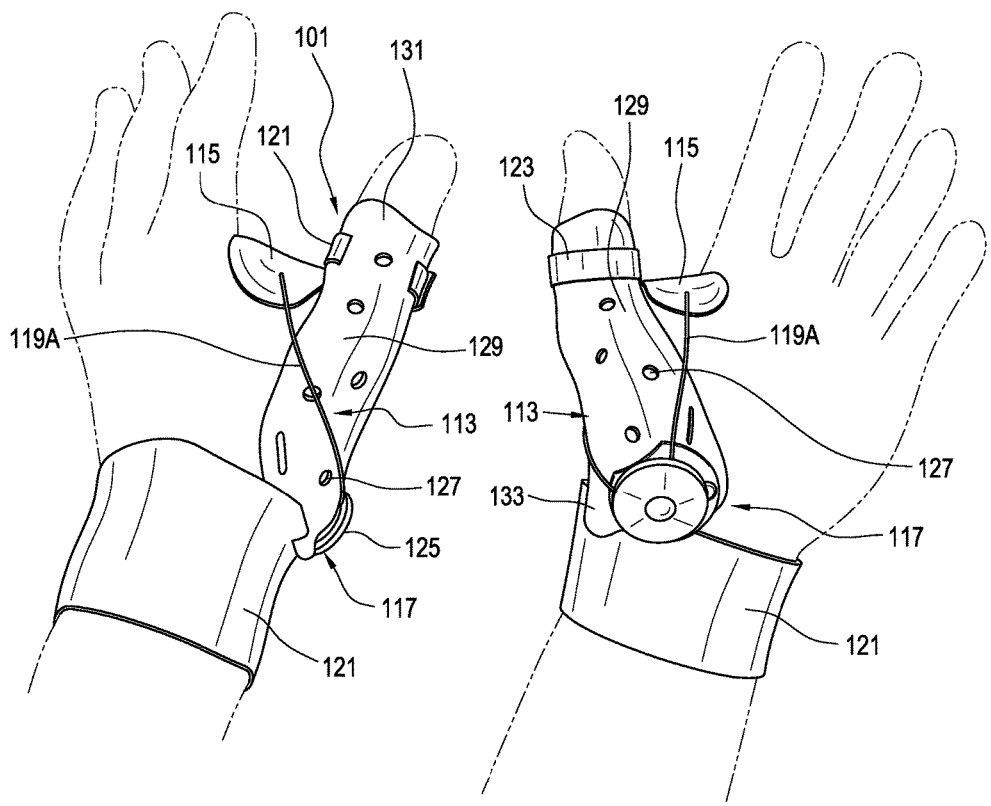
FIG. 6A is a perspective of another embodiment of a hand support showing a dorsal aspect of the hand.
FIG. 6B is a perspective view of the hand support of FIG. 6A generally showing a palmar aspect of the hand.

FIGS. 6A and 6B exemplify a variation of the hand support 101 of FIGS. 5A and 5B. The support 101 includes a base component 113 including a rigid or substantially rigid shell 129 having a thumb portion 131 arranged to encircle the thumb. The shell 129 defines a plurality of apertures 127 arranged for ventilating the shell 129, and may also be provided in sufficient quantity to impart some flexibility to the shell 129. A wrist portion 133 of the shell is arranged to extend about at least a portion of the wrist and a wrist strap 121 secures the support to the wrist and connects to the wrist portion 133. Thumb portion 131 defines a split, as in preceding embodiments, and a thumb strap 123 encircles the thumb portion 131. The thumb portion 131 extends continuously to the wrist portion 133.

A counterforce device 117 includes a tensioning device 125 connected to an elongate element 119 securing to an anchor element 115 arranged at an area between an index finger and thumb. The anchor element 115 is preferably sized and configured to generally span the distance between the base of the thumb and the base of the index finger. The dial tensioning element 125 preferably secures to a wrist portion 133 of the base component 113. The tensioning device 125 is arranged to incrementally tension the elongate element 119 and draw the anchor element 115 toward the base component 113. The elongate element 119 includes first and second portions 119A, 119B extending over dorsal and palmar portions of the hand and securing to the anchor element 115.

Figure 7:
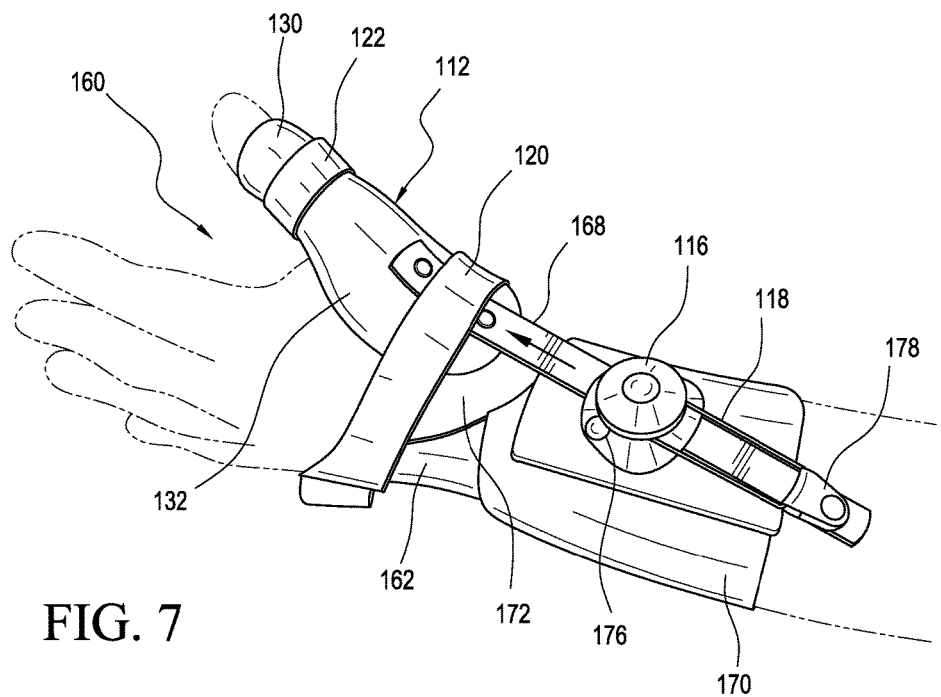
FIG. 7 is a perspective view of another embodiment of a hand support generally showing a dorsal aspect of the hand.
Figure 8:
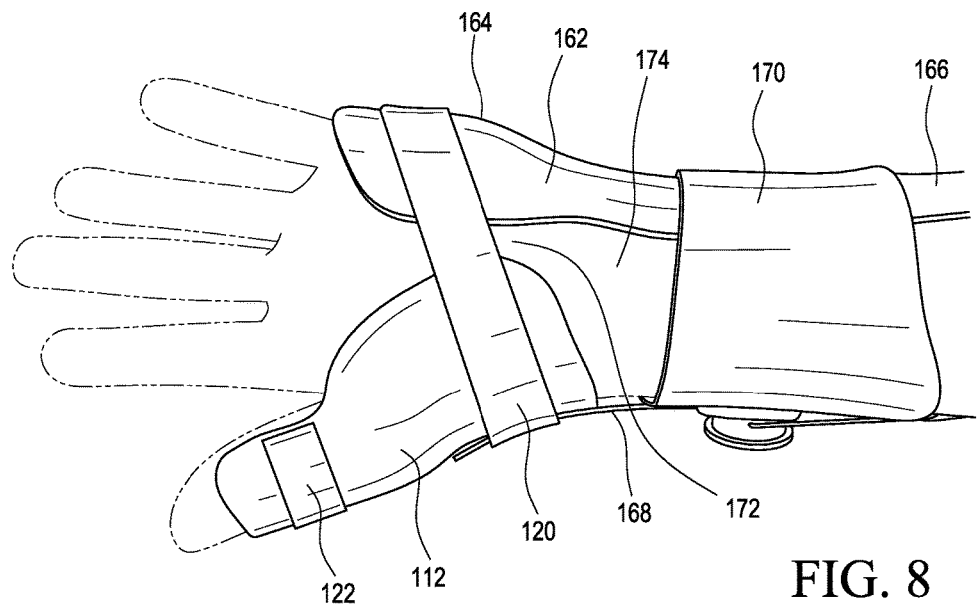
FIG. 8 is a perspective view of the hand support of FIG. 7 generally showing a palmar aspect of the hand.

As illustrated in FIGS. 7 and 8, another hand support 160 includes a base component 112 having a thumb portion 130 and a wrist portion 132 adapted to be secured about a first side of a hand and only extend over first portions of dorsal and palmar aspects of a hand. A hand support 162 is arranged to be secured to a second side of a hand and only extend over second portions of dorsal and palmar aspects of a hand. A clearance 172 is defined between the base component 112 and the hand support 162. The hand support 162 forms a distal portion 164 generally located opposed to the base component 112 and a proximal portion 166 extending beyond the base component 112.

A bar 168 connects to the base component 112 and the hand support 162. The bar 168 may extend from the base component 112 and proximally to the proximal portion 166 of the hand support 162 generally along the same side of the hand support 160.

The tensioning device 116 is slidably mounted on the bar 168 and mounted to the base component 112 by a mounting part 176. The elongate element 118 couples to the tensioning device 116 and a diverter 178 located at a proximal portion of the bar 168, such that by adjustment of the tensioning device 116, the bar 168 slides relative to the base component 112 to distract the CMC joint. The mounting part 176 may include a channel (not shown) through which the bar 168 slides.

A thumb strap 122 secures about the thumb portion 130 and a wrist strap 120 is arranged to secure about the wrist portion 132 and the hand support 162 and bridges the clearance 172. A proximal strap 170 extends proximally relative to the wrist strap 120 and over a proximal clearance 174 defined between opposed sides of the proximal portion 166 of the hand support 162.

Figure 9:
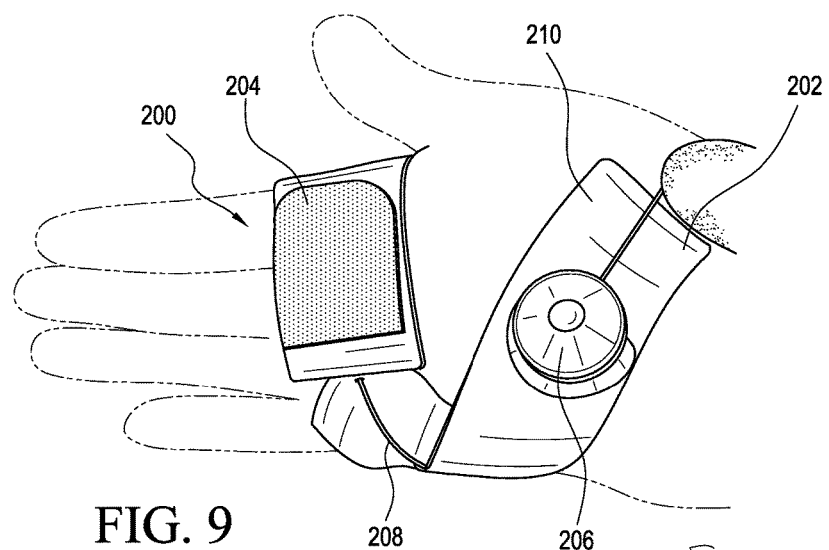
FIG. 9 is a perspective view of another embodiment of a hand support generally showing a dorsal aspect of the hand.
Figure 10:
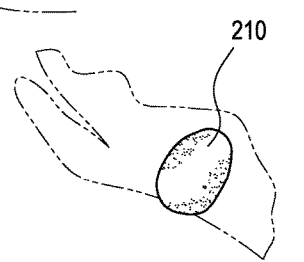
FIG. 10 is a perspective view of a bolster for use in the embodiment of FIG. 9.

FIGS. 9 and 10 exemplify another hand support 200 having a base component 202 arranged to secure to a wrist, an anchor element 204 adapted to extend between or at an index finger and a thumb, and a counterforce device 206 secured to the base component 202 and coupling the base component 202 to the anchor element 204 by an elongate element 208 secured to the anchor element 204. The counterforce device 206 is arranged to incrementally tension the elongate element 208 and draw the anchor element 204 with the elongate element 208 spiraling about the wrist. The base component 202 is adapted to secure and extend about a wrist and spiral over the dorsal aspect of the hand. The elongate element 208 extends over the base component 202. A bolster 210 is arranged for placement between the base component 202 and the wrist of the hand proximate the first carpal-metacarpal joint.

Figure 11:
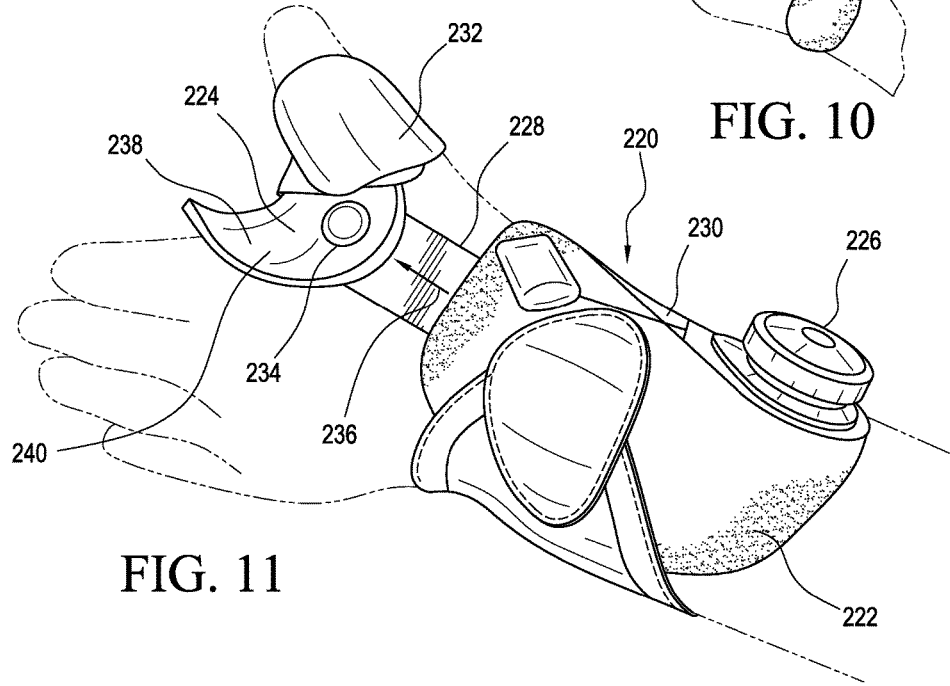
FIG. 11 is a perspective view of another embodiment of a hand support generally showing a dorsal aspect of the hand.
Figure 12:
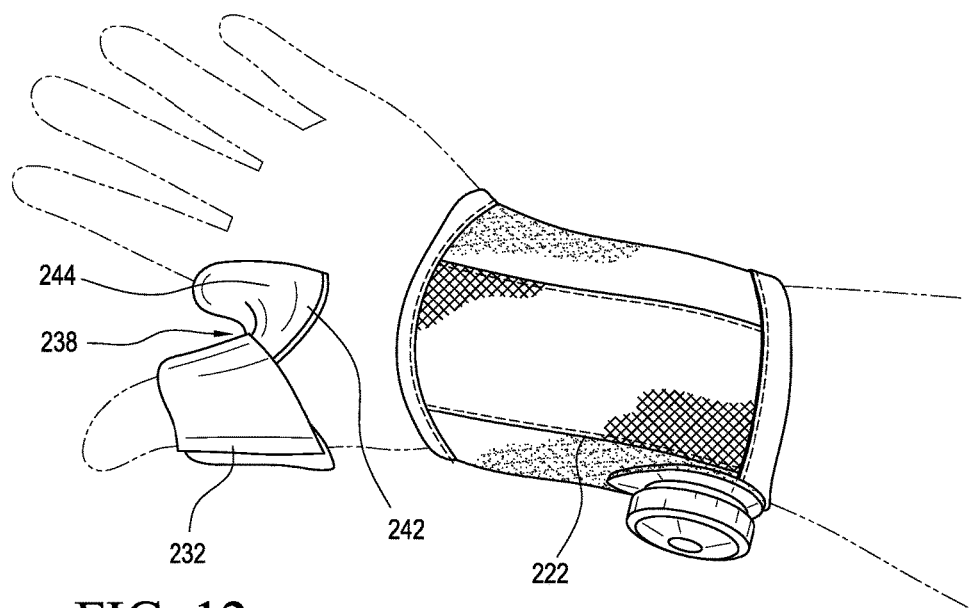
FIG. 12 is a perspective view of the hand support of FIG. 11 generally showing a palmar aspect of the hand.

FIG. 11 shows another hand support 220 having a base component 222 arranged to secure to a wrist, an anchor element 224 extending between or at an index finger and a thumb, and a counterforce device 226 secured to the base component 222 and coupling the base component 222 to the anchor element 224 by an elongate element 230 secured to the anchor element 224. A bar 228 connects to the anchor element 224 and couples to the elongate element 230 such that the bar 228 is adjustably secured to move in a direction 236 toward the anchor element 224.

A digit retainer 232 is secured to the anchor element 224 and is adapted to secure about a thumb. The anchor element 224 defines a saddle 238 extending between the thumb and the index finger. The anchor element 224 is substantially rigid and maintains the saddle profile 238 anatomically contouring to the space. The saddle profile 238 has a dorsal portion 240, a palmar portion 242 and a bridging portion 244 between the dorsal and palmar portions 240, 242.

The bar 228 pivotally attaches to the anchor element 224 by a pin 234. The counterforce device may be a tensioning device 226 and may be operatively engaged with the bar 228 in a manner similar to the embodiment of FIGS. 7 and 8.

Figure 13:
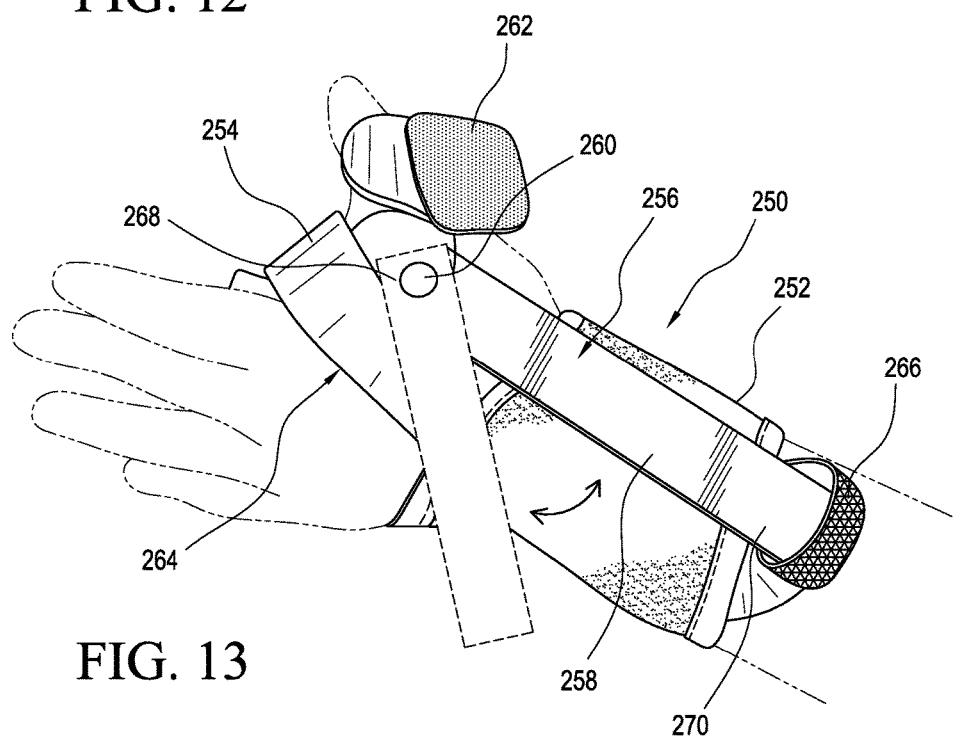
FIG. 13 is a perspective view of another embodiment of a hand support generally showing a dorsal aspect of the hand.

FIG. 13 depicts another hand support 250 embodiment including a base component 252 arranged to secure to a wrist, an anchor element 254 arranged extend between or at an index finger and a thumb, and a counterforce device 256 selectively secured to the base component 252 and pivotally connected to the anchor element 254.

The counterforce device 256 includes a bar 258 connected to the anchor element 254 by a pin 260 at a first end 268 such that the bar 258 has a second end 270 opposite the first end 268 and rotatable relative to the pin 260 such that rotation of the bar 258 is arranged to pull a metacarpal joint apart.

A retainer 266 may be mounted on the base component 252 and adapted to retain the second end 270 of the bar 258. A digit retainer 262 connects to the anchor element 254 to retain the thumb. A joining strap 264 is arranged to extend over dorsal and palmar portions of the hand and over or along the anchor element 254 and secure to the base component 252.

Figure 14:
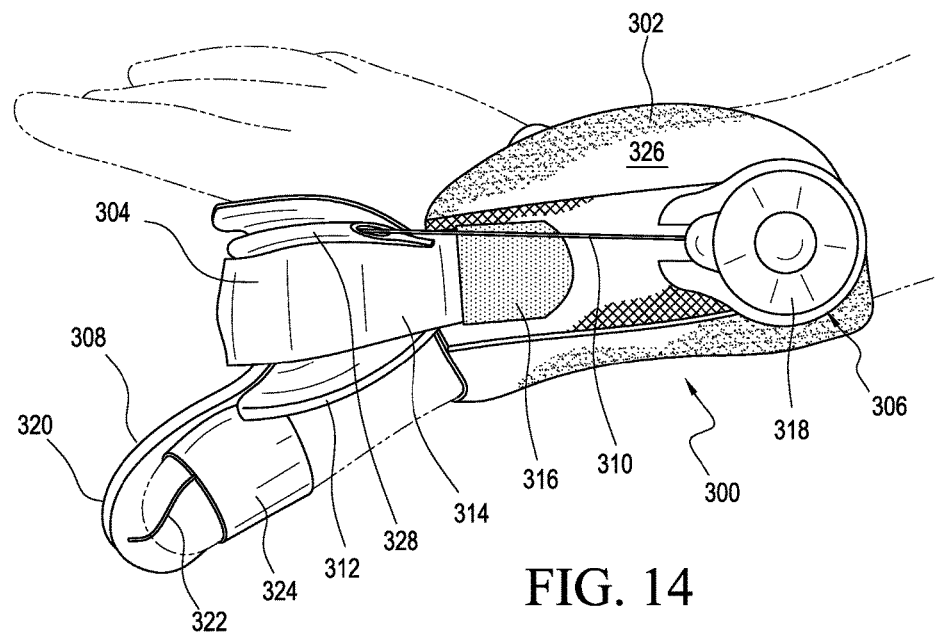
FIG. 14 is a perspective view of another embodiment of a hand support generally showing a dorsal aspect of the hand.

FIG. 14 illustrates yet another hand support 300 having a base component 302 arranged to secure to a wrist, an anchor element 304 arranged extend between or at an index finger and a thumb, a counterforce device 306 secured to the base component 302 and adjustably connected to the anchor element 304, and a digit retainer 324 arranged for gripping a thumb. The digit retainer 324 is connected to a bar 308 by a tether 322 extending from an end 320 of the bar 308 a distance to suspend the digit retainer 324 therefrom.

The bar 308 is secured to the anchor element 304, such that adjustment of the counterforce device 306 adjusts suspension of the digit retainer 324 relative to the base component 302.

The counterforce device 306 is arranged to incrementally tension an elongate element 310 connected to the anchor element 304 and draws the anchor element 304 toward the base component 302. The counterforce device 306 includes a tensioning device 318 secured to the base component 302. A tube 328 extends over or along the anchor element 304.

The anchor element 304 includes a saddle 312 extending between a space formed between the thumb and the index finger. The saddle 312 may be rigid or substantially rigid.

A joining strap 314 has first and second ends connecting to the base component 302 and extends over or along the anchor element 304. The first end of the joining strap 314 has a tab 316 removably securing to a surface 326 of the base component 302.

Figure 15:
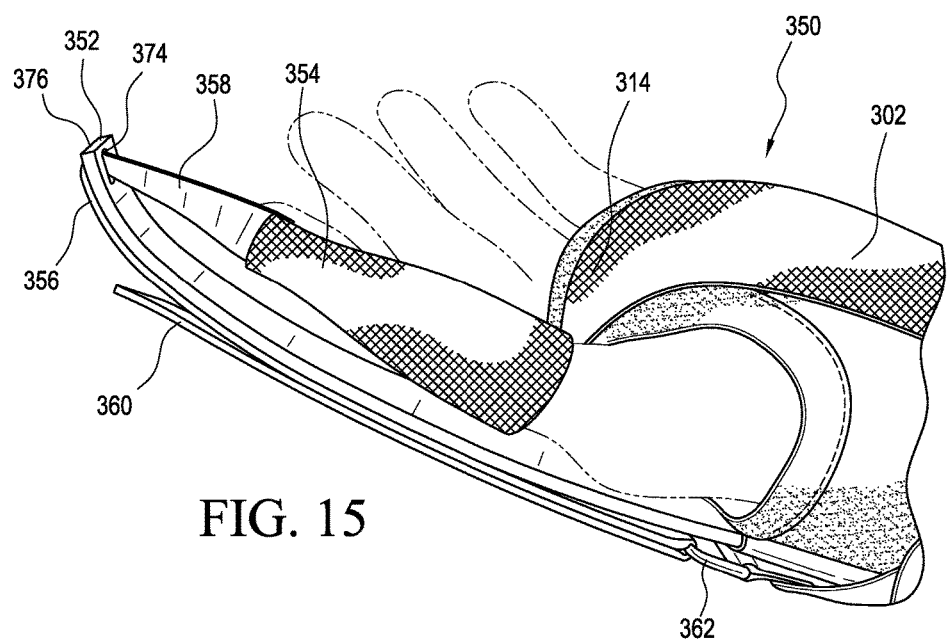
FIG. 15 is a perspective view of another embodiment of a hand support generally showing a palmar aspect of the hand.
Figure 16:
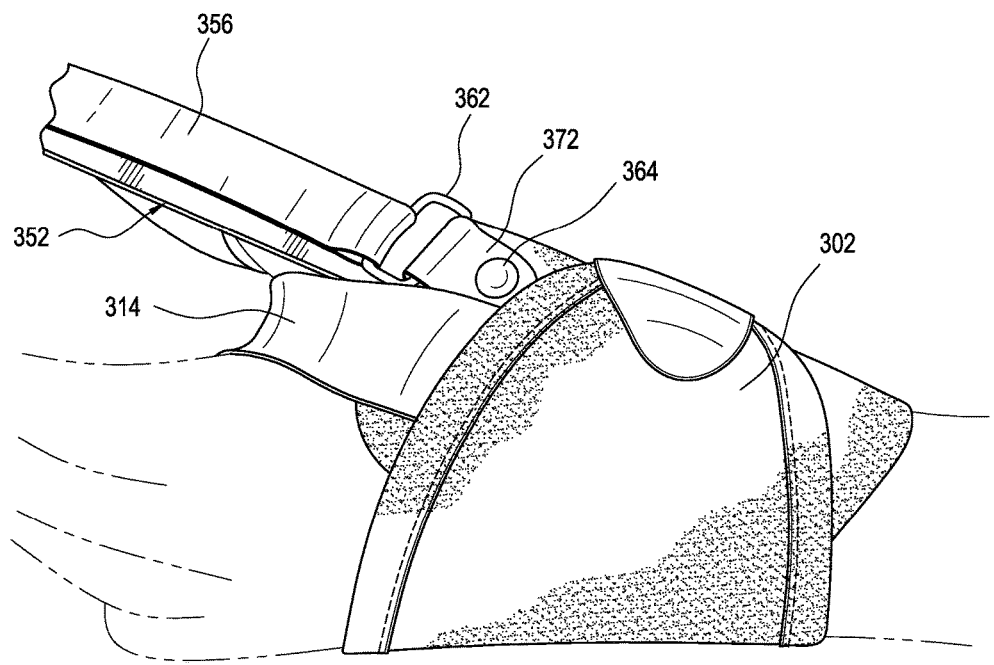
FIG. 16 is a perspective view of the hand support of FIG. 15 generally showing a dorsal aspect of the hand.

Referring to the hand support of FIGS. 15 and 16, a base component 302 is arranged to secure to a wrist, an anchor element 304 arranged to grip a digit, and a counterforce device 306 secures to the base component 302 and the anchor element 304.

The counterforce device 306 includes a bar 352 connected to the base component 302. A strap 356 has a first portion 358 cantilevered at a first section 376 of the bar 352. A digit retainer 354 connects to the first portion 358 of the strap 356. The strap 356 is adjustable to modify a length of the tethering portion 358 between the first section 376 of the bar 352 and the digit retainer 354. The bar 352 may be substantially rigid and resilient to generally maintain a configuration depending on adjustment of the strap 356.

A buckle 362 is provided through which a second portion 360 of the strap 356 extends. The second portion 360 is arranged to secure to itself according to length adjustment of the first portion 358. The buckle 362 is pivotally attached to the bar 352 by a tab 372 carrying the buckle 362 and a pin 364 attached to the bar 352. The bar 352 may have a second section 366 adapted for being received by the base component 302 and securing therewith.

Figure 17:
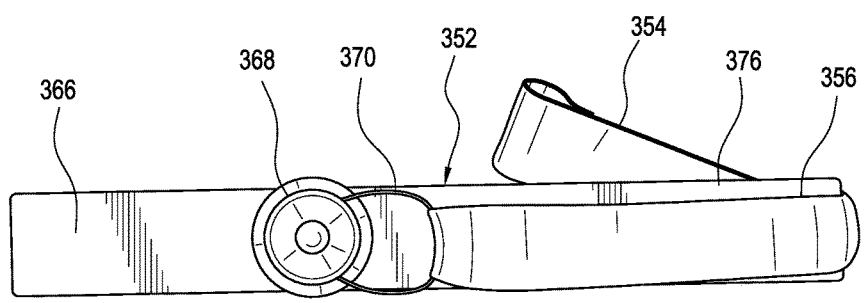
FIG. 17 is a perspective view of a counterforce device and anchor useable in the hand support of FIG. 15.
Figure 18:
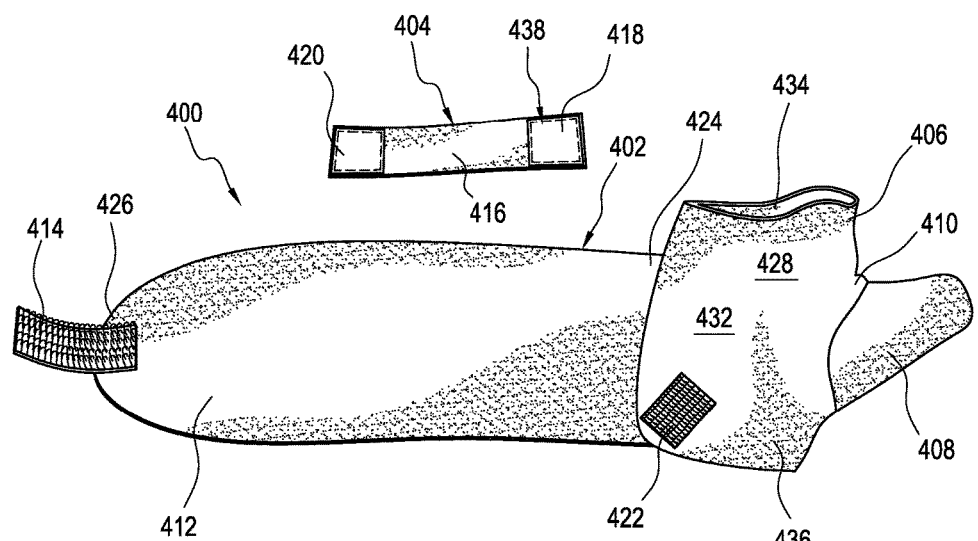
FIG. 18 is a plan view of a hand support in an open configuration.

In a variation of the hand support 350 in FIG. 17, a tensioning device 368 mounts to the bar 352 and an elongate element 370 engages the tensioning device 368 and secures to a second portion 360 of the strap 356 for adjusting the length of the first portion 358 between the bar 352 and the digit retainer 354. The bar 352 may define a slot 374 located at the first section 376 of the bar 352 through which the strap 356 extends. The digit retainer 354 is a finger trap arranged to seize control of a digit upon pulling by the strap 356, such as a "Chinese handcuffs."

FIGS. 18-24 depict a flexible and soft hand support 400 that does not include traction means. This hand support 400 embodiment may be used in earlier stages of hand arthritis to provide support, compression and protection. The hand support is versatile in that it can be used to treat a variety of hand deficiencies and movements.

The hand support 400 has a main body 402 arranged to extend about a hand. The main body defines a hand section 406 and a thumb section 408 bordered by a bridging section 410. A flap 412 extends from the main body 402 and is adapted to wrap and secure to the main body 402. A first end 424 of the flap 412 secures to the hand section 406 and extends to a second end 426 carrying a tab 414 arranged to secure to a surface 428 of the hand section 406. An auxiliary strap 404 is arranged to secure over the surface of the main body 402 in a plurality of locations and orientations.

The hand section 406 forms a sleeve through which palmar and dorsal sides of a hand extend. The thumb section 408 forms a tube through which a thumb extends, and the bridging section 410 separates the thumb section 408 from the hand section 406. The thumb section 408 is arranged to extend obliquely relative to the hand section 406.

The material forming the main body 402 may be elastic to gently conform to the anatomy of the hand. The main body 402 preferably includes a body tab 422 on a palmar portion 432 of the hand section 406 arranged to secure to the flap 412.

The material forming the flap 412 may be elastic so as to tension over the main body 402 and conform to the hand. The flap 412 preferably has a length arranged to encircle at least once an entirety of the main body 402 by extending over both dorsal and palmar portions 430, 432.

At least a substantial entirety of the surface 428 of the main body 402 has hook receivable material and is substantially elastic.

The auxiliary strap 404 preferably defines an elongate segment 416 bordered at opposed ends 418, 420 by fasteners. The elongate segment 416 of the auxiliary strap 404 is substantially inelastic, and the fasteners 438 are arranged to engage the hook receivable material of the main body 402 entirely between top and bottom portions 434, 436 of the main body 402.

Figure 19:
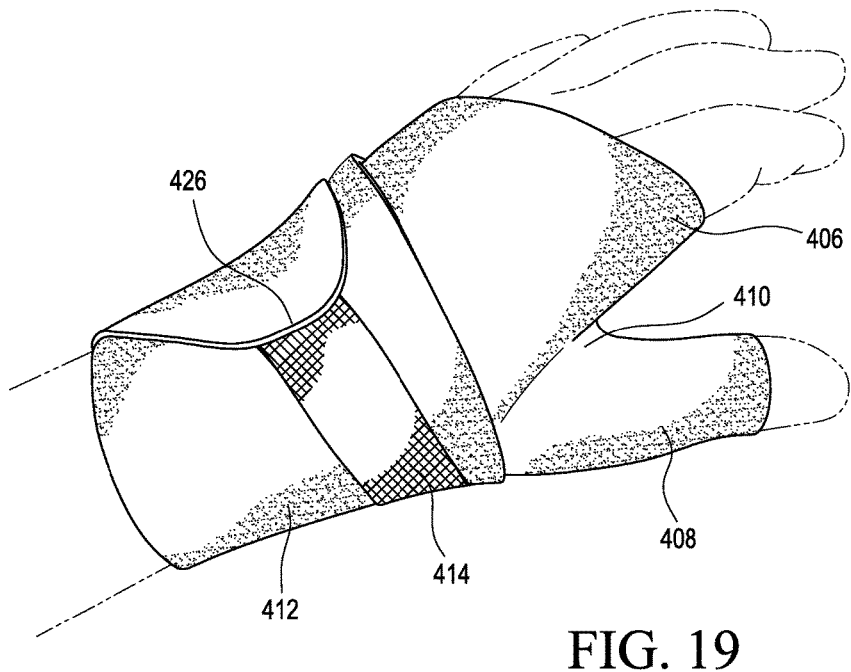
FIG. 19 is a perspective view of the hand support of FIG. 18 in a closed configuration.

Referring to FIG. 19, the hand support 400 is applied to the hand and the flap 412 is in a closed configuration to wrap about the main body 402 on the hand. The flap 412 tensions as it is wrapped to secure to the main body 402 on the hand and provide compression for the hand.

The auxiliary strap 404 is detachable from the hand support 400 and advantageously allows for placement over the entirety of the surface of the main body 402 and the flap 412. Because of this versatility, the hand support 400 is capable of being adapted to orient the hand in manner orientations for supporting and treating the hand.

Figure 20:
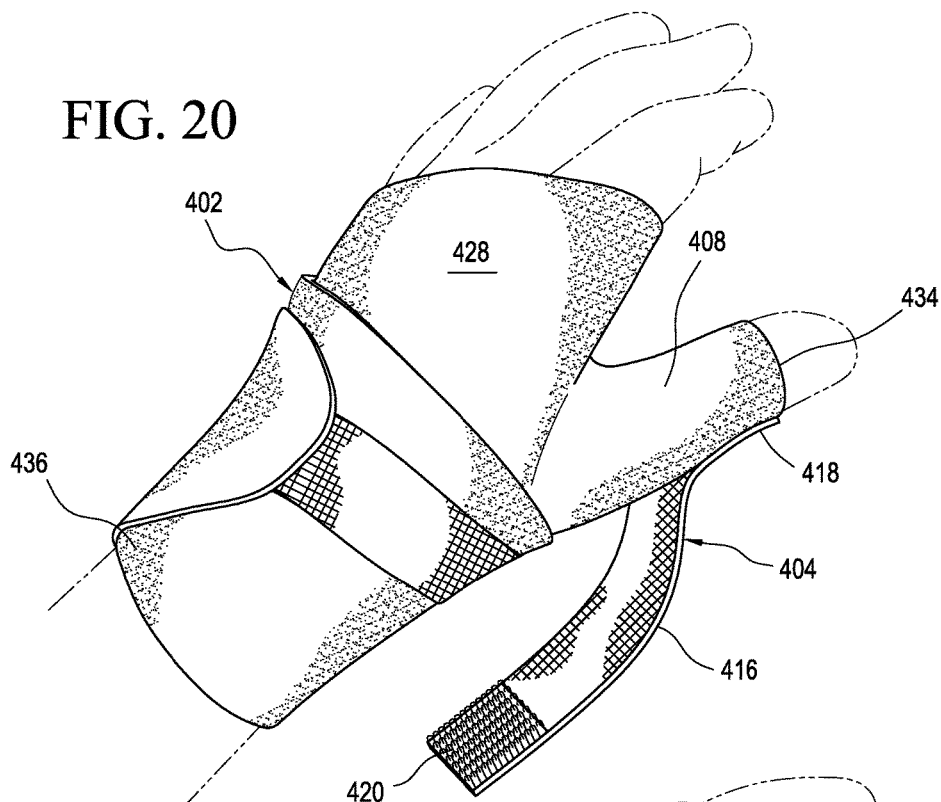
FIG. 20 is a schematic view showing installation of an auxiliary strap on the hand support of FIG. 18.
Figure 21:
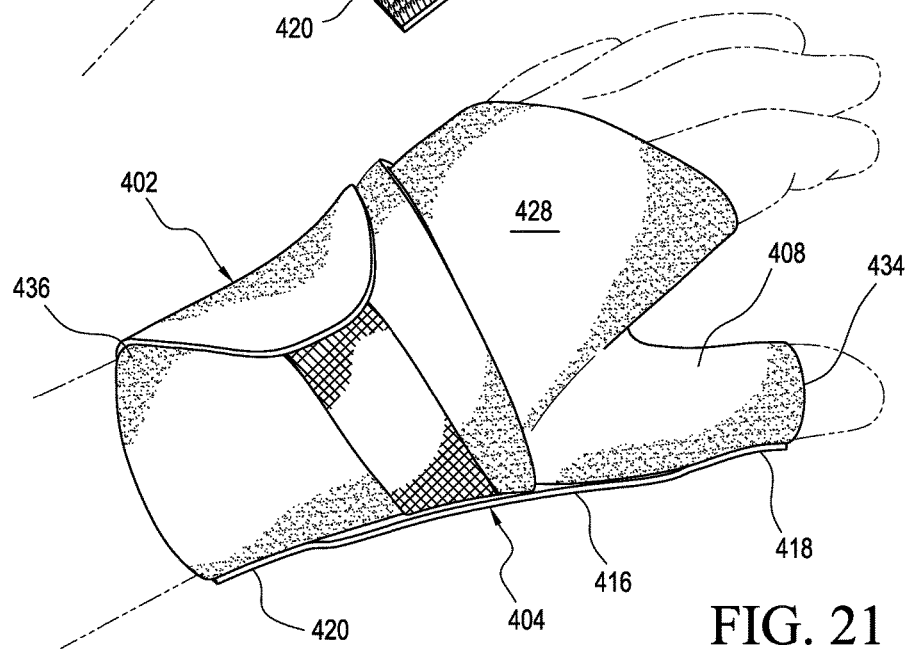
FIG. 21 is a schematic view of FIG. 20 with the auxiliary strap placed to radially abduct the thumb.

FIGS. 20 and 21 depict application of the auxiliary strap 404 on the thumb section 408 to radially abduct the thumb. Application of the auxiliary strap 404 may include placement of the first tab 418 at a predetermined location and then the auxiliary strap 404 is tensioned with the second tab 420 being secured at another location to radially abduct the thumb.

Figure 22:
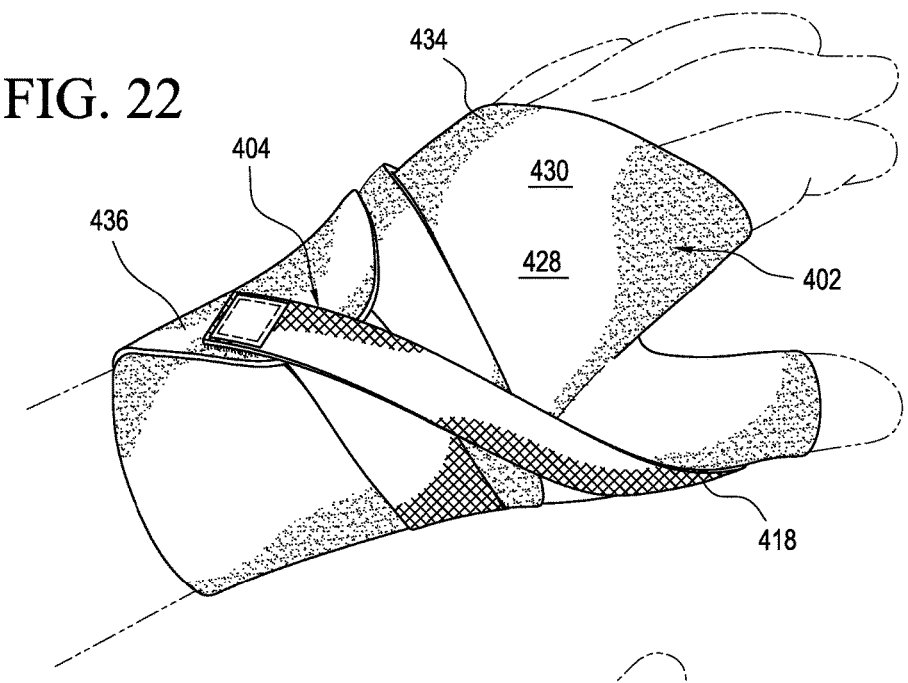
FIG. 22 is a schematic view of FIG. 20 with the auxiliary strap placed to palmar adduct the thumb.
Figure 23:
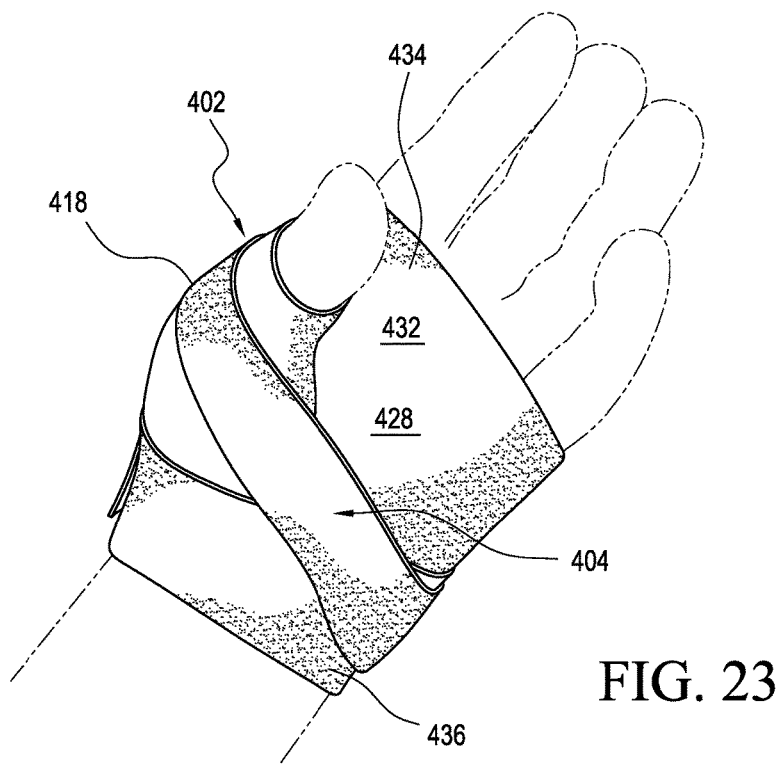
FIG. 23 is a schematic view of FIG. 20 with the auxiliary strap placed to radially abduct the thumb.
Figure 24:
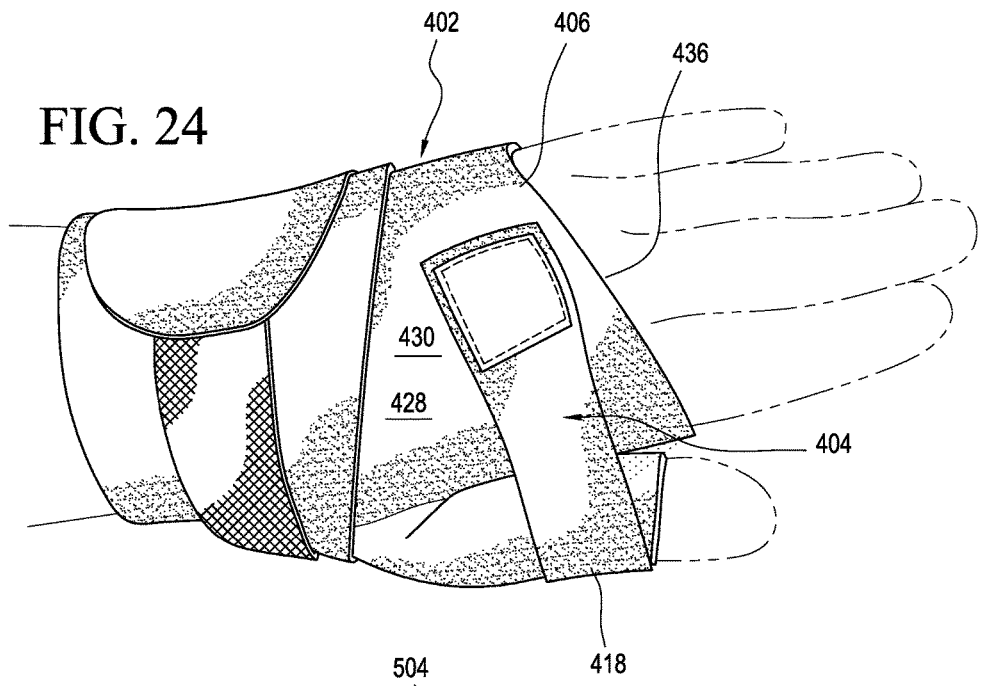
FIG. 24 is a schematic view of FIG. 20 with the auxiliary strap placed to radially adduct the thumb.
Figure 25:
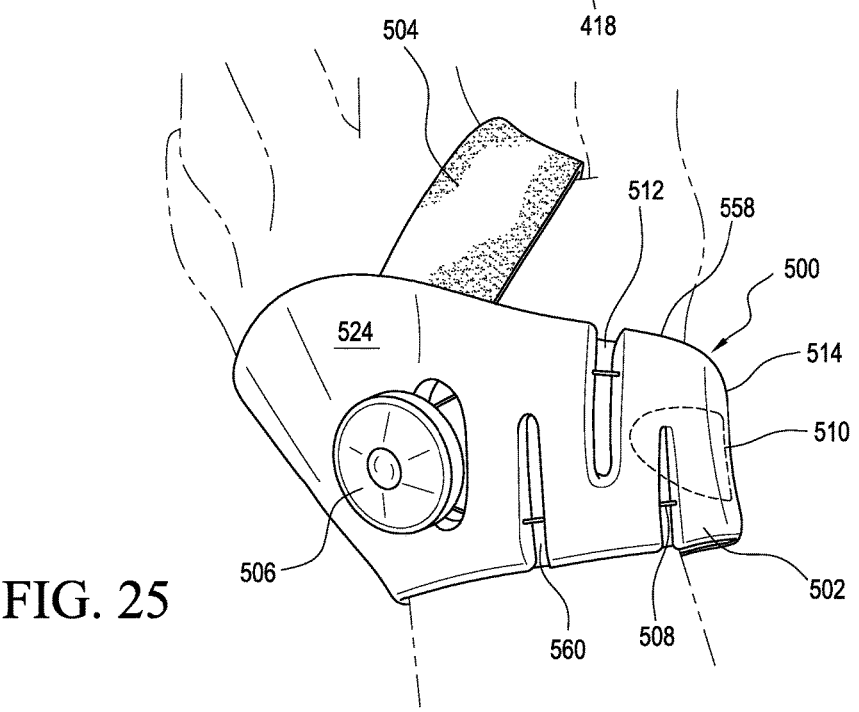
FIG. 25 is a perspective view showing another hand support embodiment.

FIG. 22 shows how the auxiliary strap 404 can be placed over the palmar aspect of the hand support to palmar adduct the thumb. FIG. 23 exemplifies how the auxiliary strap can be placed to palmar abduct the thumb. FIG. 24 illustrates how the auxiliary strap can be placed to radially adduct the thumb.

Referring to FIGS. 25-28, another hand support 500 is provided to exert pressure over the CMC joint with a bolster 510 arranged to press into and lift up the CMC joint. A wrist strap 514 is tensionable and the bolster 510 is preferably located along an inner side 516 of the wrist strap 514. A plurality of bolsters 528, 530, 532 may be provided depending on the level of pressure the bolster is intended to exert and for treatment stages to engage a localized section of the hand or wrist.

The hand support 500 includes a base component 502 arranged to secure to a wrist and defining at least one opening 512 formed along a portion of the length of the base component 502 and extending from a periphery 558 into a width of the base component 502. An anchor element 504 is arranged to extend between or at an index finger and a thumb. A counterforce device 506 is secured to the base component 502 and comprises at least one elongate element 508 linked to the counterforce device 506 and cooperating with the base component 502 to adjust the length thereof by actuation of the counterforce device 506.

The base component may be constructed in an accordion manner, similar to the buttress described and illustrated in co-pending U.S. provisional application No. 62/058,306, filed Oct. 1, 2014, and incorporated herein by reference. The counterforce mechanism can be similar to the tensioning device in U.S. provisional application No. 62/058,306.

At least one elongate element 508 travels through a thickness 560 of the base component 502 and extends to a strap clip 518 located at a first portion of the base component 502. The base component 502 defines a strap segment 514 between at least the counterforce mechanism 506 and the strap clip 518. The strap clip 518 releasably secures to a strap coupler 520 located at a second portion of the base component 502.

The anchor element 504 is a preferably a strap extending between palmar and dorsal portions 524, 526 of the base component 502 such that a first portion of the anchor element releasably secures to a fastener 522 located on the base component 502. The anchor element 504 may be releasably secured at opposed first and second portions of the base component 502, or secured and tensionable by other known methods such as rings and buckles.

Figure 26A:
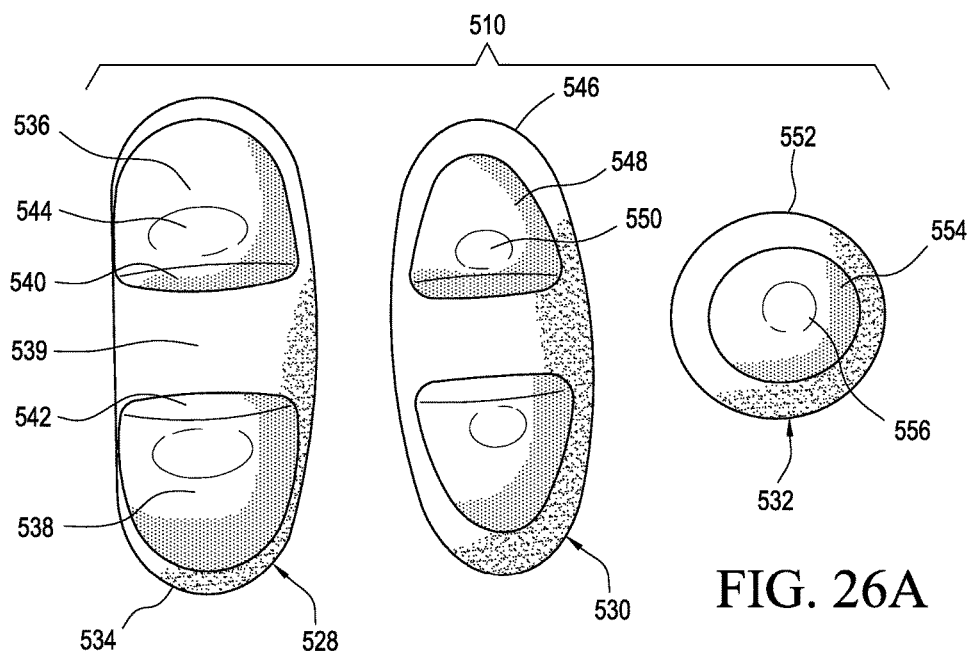
FIGS. 26A and 26B are schematic views showing a set of bolsters for use in the hand support of FIG. 25.
Figure 26B:
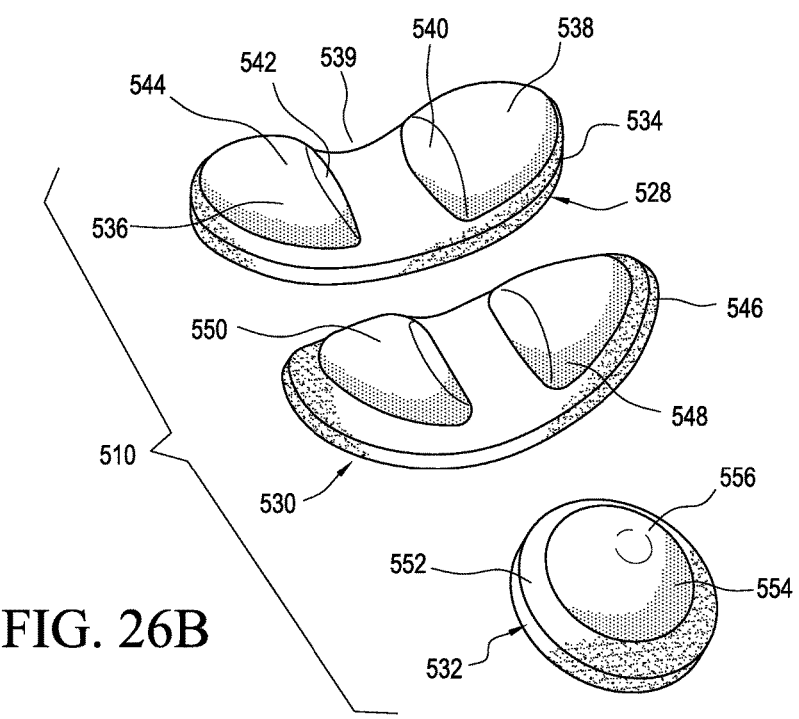

As illustrated in FIGS. 26A and 26B, a plurality of bolsters 528, 530, 532 have different pad configurations for engaging a localized section of the hand or wrist and securing to an inner surface 516 of the base component 502. For example, a first bolster 528 includes a main layer 534 selectively securable to an inner surface 516 of the base component 502. The bolster 528 has a pair of pads 536, 538 protruding from the main layer 534 and each pad forms a point 544 having a configuration for engaging the hand or wrist. The pads 536, 538 are preferably spaced apart by a clearance 539 so as to enable space for placing a joint of the hand or wrist therebetween. Side supports 540, 542 are located on opposed sides of the clearance 539 for engaging the hand or wrist, and are anatomically shaped to grasp the joint.

The sizes and pad configurations of the bolsters 528, 530, 532 may vary among each bolster. For example, the configuration of the bolster 528 includes larger pads 536, 538 that are adapted to embrace the joint and lift it upwardly for traction. The main layer 534 is preferably relatively long and broad to enable the embracing function, along with wider and larger points 544 on each pad 536, 538.

Referring to the bolster 530, this arrangement includes pads 548 having sharper points 550. The pads 548 are configured as being steeper and may rise to generally the same height as the pads 544 in the bolster 528. The bolster 530 is arranged to press more into each side of the joint and lift it upwardly. The bolster 532 is arranged with a single pad 554 having a single point 556 raising a height that may be similar to the height of the pads of the bolsters 528, 530. The bolster 532 is arranged to press into the joint and lift it upwardly. The main layers 546, 552 are configured and dimensioned according to the arrangement of the pads of the individual bolsters 530, 532, respectively.

Figure 27:
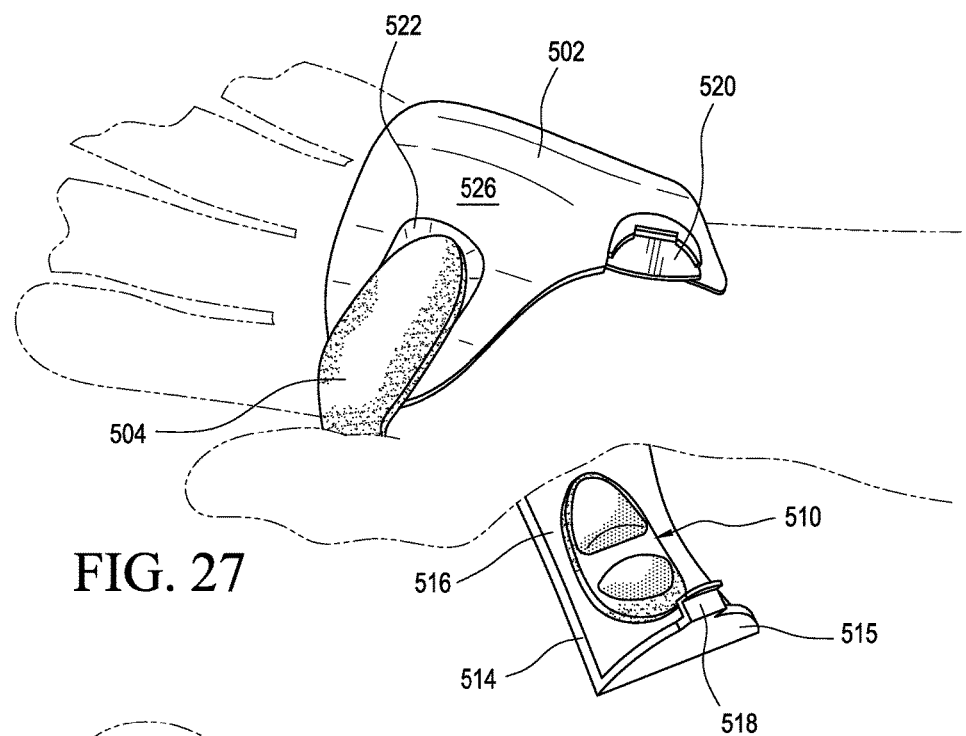
FIG. 27 is a perspective view of the hand support of FIG. 25 in an open configuration with a bolster.

Referring to FIG. 27, the bolster 510 may be selectively arranged along the inner layer 516 of the base component 502. The inner layer 516 may have a hook-receivable surface and is separate from the material forming an outer layer 515 of the base component 502. The outer layer 515 may be a foam-based or molded material having the openings 512. The outer layer 515 is preferably resilient in that it returns to an original, predetermined shape when there is minimal tension in the elongate element 508.

The outer and inner layers 515, 516 may be separate from one another except at end portions like at the strap clip 518 and strap buckle 520, such that tensioning of the elongate element 508 causes the outer layer 515 to tension and compress over the inner layer 516 without substantially increasing tension in the inner layer 516. Alternatively, the outer and inner layers 515, 516 may be secured to one another along their length.

Figure 28:
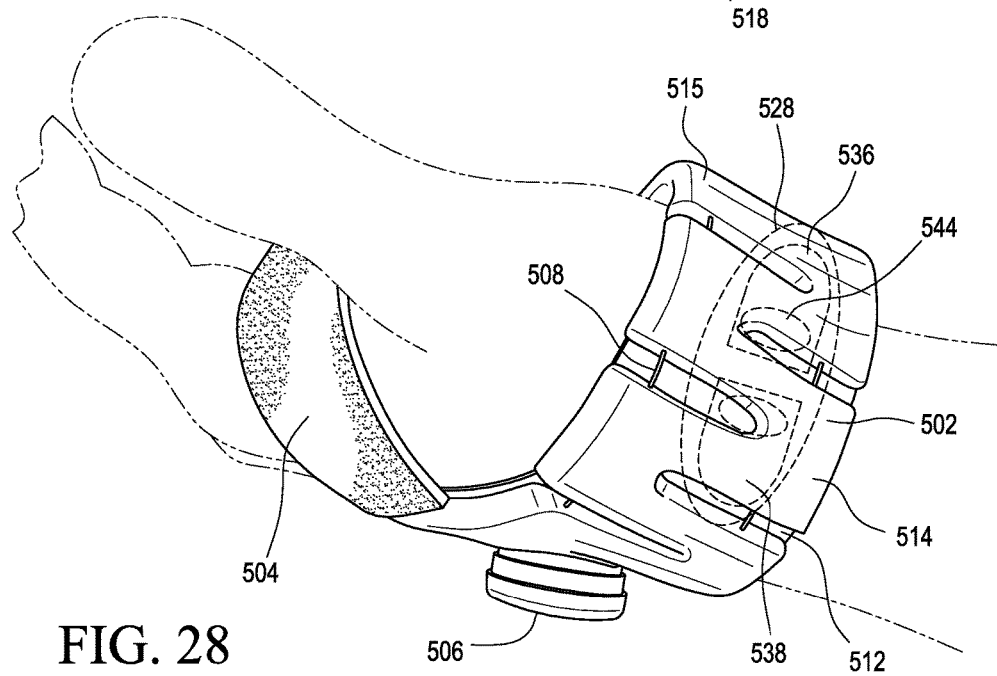
FIG. 28 is a schematic view showing placement of the bolster in the hand support of FIG. 25 in a closed configuration.

In use, as shown in FIG. 28, the base component 502 is tensioned about the wrist with the bolster 528 interposed between the base component 502 and the wrist. The anchor element 504 travels between the index finger and the thumb, and secures at both ends to the base component 502. The counterforce mechanism 506 is tensioned to contract the openings 512 of the wrist strap 514 formed by the base component 502, and exert compression of the bolster 528 against the joint. The points 544 of the pads 536, 538 embrace the joint, particularly due to the tensioning of the counterforce mechanism 506 and tensioning of the wrist strap 514, and lift the joint upwardly for treatment.

Referring to the embodiments of FIGS. 29A and 29B, a hand support 600 comprises a base component 602 arranged for securing about a hand or wrist, a joint stabilizer 604 secured or mounted to the base component 602, an elastic element 606 extending from the joint stabilizer 604 at a first end 610, and a retainer 608 securing to a second end of the elastic element 606 and adapted to secure along a thumb preferably below a thumb knuckle K. The elastic element 606 is arranged to bias between the retainer, which snugly secures to the thumb without movement as a result of biasing of the elastic element, and the joint stabilizer 604.

The base component 602 preferably includes a strap 603 enabling tightening about the wrist and hand of the wearer. The base component 602 includes an opening 605 adapted for insertion of a thumb. A reinforcement component 616 is secured to the strap and formed of a more rigid material than the base component 602. The reinforcement component 616 preferably has a bridging portion 618 extending over the thumb web of the hand to maintain spacing of the base component 602. The reinforcement component 616 may be a flexible plastic, such as a thermoplastic enabling rigidity when the strap 603 is tightly secured to the hand yet some flexibility to enable adjustment about the hand when the strap 603 is loosened for setting of the hand support 603 for an individual user.

The joint stabilizer 604 is preferably more rigid than the reinforcement component but rather than merely being flexible, it may be malleable for pinching or securing about the thumb at a location preferably about the CMC joint to create a tight fit over the thumb. When muscles contract under the joint stabilizer 604, they become larger in circumference and an expansion force is directed inwardly, increasing pressure to stabilize the bone within the contained space of the support 600.

The joint stabilizer 604 has first and second ends 609, 611 extending from a base portion 607. The base portion 607 is preferably thicker or includes more material to provide a substantially more dimensionally stable portion of the joint stabilizer, whereas the first and second ends 609, 611 may be thinner so they can be more malleable. Despite taking advantage of the malleability of the joint stabilizer, once adjusted manually, the joint stabilizer maintains its shape on the hand or about the thumb of the user. Substantial force is required for adjusting the shape of the joint stabilizer beyond normal use of the joint stabilizer on the hand of a user.

While a preferred material for the joint stabilizer 604 is aluminum, other materials may be used. The joint stabilizer 604 may be configured as a solid structure, as depicted, or alternatively may be formed as bands or a mesh-like configuration to better contour to the anatomy of a hand and reduce the weight and profile of the hand support.

The joint stabilizer 620 defines a generally J-shape, with a first end 624 having a taper for mounting about a dorsal aspect of a hand, and a second end 626 adapted for wrapping about at least part of a palmar aspect of a hand. The first and second ends 624, 626 extend from a base portion 622 extending about a base of a thumb between the dorsal and palmar aspects of the hand. As noted above, the joint stabilizer 620 is adapted so the first and second ends 624, 626 are moveable relative to the base portion 622 for embracing the CMC joint, and remaining in position when secured to the hand of the user.

The first end 610 of the elastic element 606 secures to either the joint stabilizer 604 or reinforcement component 616, and encircles the thumb at a location preferably below the knuckle of a user whereat the retainer 608 encircles or grasps the thumb. In the illustrated example, the elastic element 606 is a spring arranged to bias between the joint stabilizer 604 and the retainer 608. The elastic element 606 provides traction of the thumb according to other embodiments described herein. The joint stabilizer 604 may be detachable from the joint stabilizer or reinforcement component 616 to enable positioning about the thumb of the user, or may be permanently secured to the joint stabilizer or reinforcement component 616.

The retainer 608 is arranged to encircle or at least securely grasp the thumb, preferably below the knuckle of the user. The retainer 608 may include interior padding or a wedge 614 that secures the retainer at a desired location on the thumb. The retainer 608 may be a ring or may be split for opening and closing like a clamshell or clamp about the thumb for donning the hand support on the hand of a user.

Figure 29A:
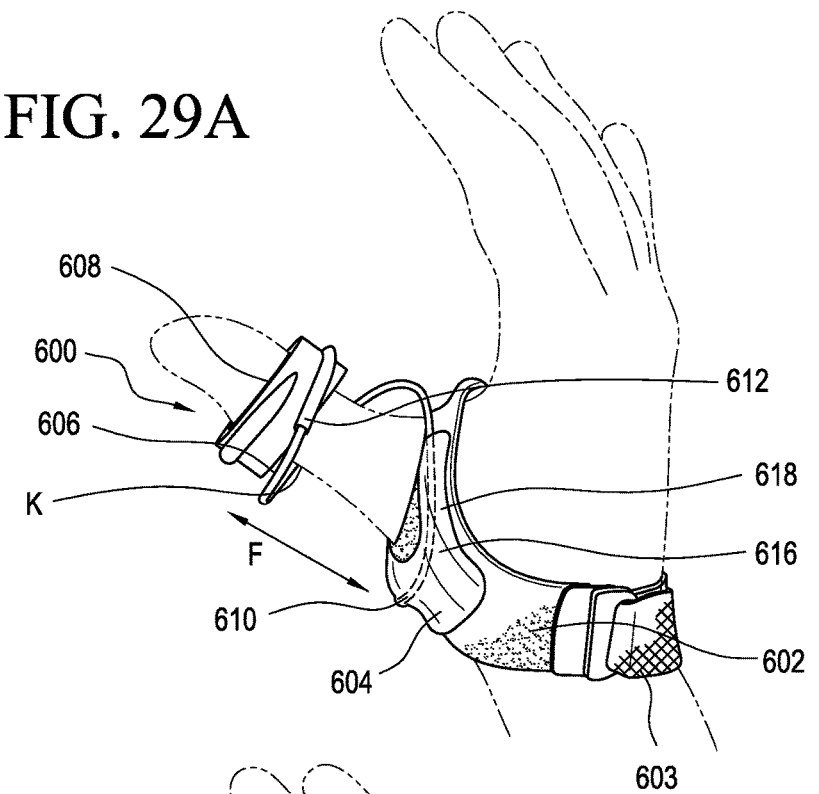
FIG. 29A is a perspective view of a thumb support.
Figure 29B:
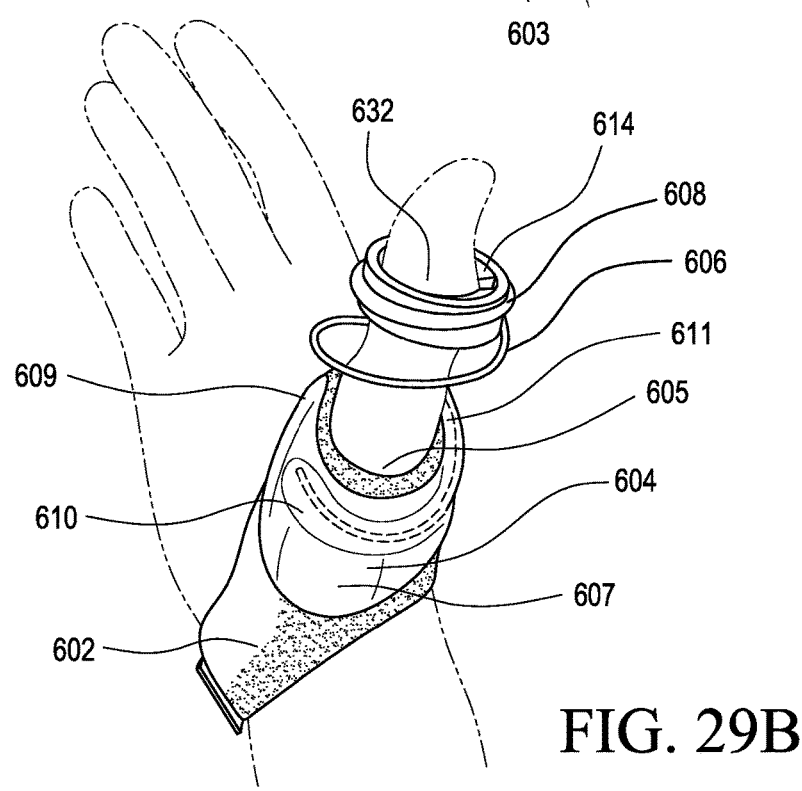
FIG. 29B is another perspective view of the thumb support of FIG. 29A.
Figure 30A:
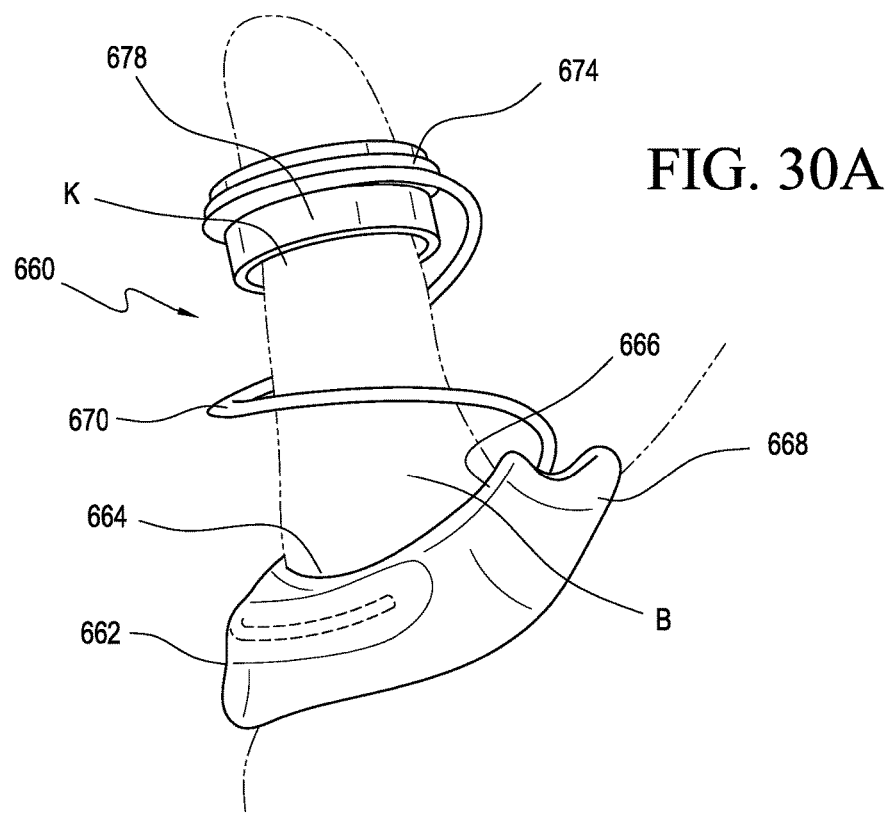
FIG. 30A is a perspective view of a thumb support.
Figure 30B:
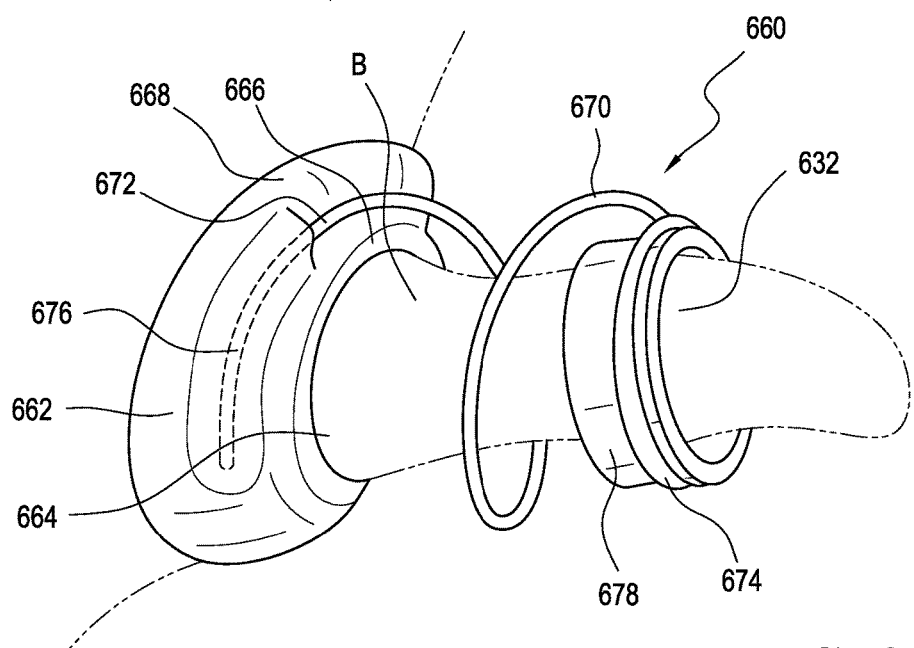
FIG. 30B is another perspective view of the thumb support of FIG. 30A.

FIGS. 30A and 30B exemplify another embodiment of a hand support 660. According to this embodiment, the hand support 660 comprises a base component 662 arranged for securing about a base of a thumb. The base component 662 defines an opening 664 and a neck 666 bordering about the opening 664 that allows for the base component 662 to snugly fit about the base of a thumb B. The base component 662 includes a shoulder 668 for stabilizing the base component 662 about the thumb and distributing pressure about the thumb. An elastic element 670 extends from the base component 662 at a first end 672 and is anchored thereto by an anchor 676. The elastic element 670 extends to a retainer 678 securing to a second end 674 of the elastic element 670 and adapted to secure along a thumb preferably below a thumb knuckle K. The elastic element 670 is arranged to bias between the retainer 678, which snugly secures to the thumb without movement as a result of biasing of the elastic element 670, and the base component 662. The hand support 660 operates similarly to the hand support 600 in the embodiment of FIGS. 29A and 29B.

In the example shown in FIGS. 31 and 32, a variation of the joint stabilizer 620 may be formed from thermoformed foam or polymeric material that is reinforced with internal malleable elements, such as wires, plates, rods, etc. The joint stabilizer 620 may generally be formed as a pad and the internal malleable elements can adjust the shape of the joint stabilizer. The joint stabilizer 620 serves as both the joint stabilizer and a reinforcement component in a combined component. A strap may be secured to the joint stabilizer 620 in a similar fashion as in the embodiment of FIG. 29A. The joint stabilizer 620 may be generally adjustable along a contour 628, which may also be formed for receiving a first end of the elastic element 606.

As shown in FIG. 32, the joint stabilizer 620 preferably rests in the palm of a hand and the thumb is insertable through the opening 621. Traction force provided by the elastic element 606 terminates at the joint stabilizer which is configured in shape to distribute pressure without moving relative to the thumb.

Referring to FIG. 31, the elastic element 606 is generally spiral in configuration between first and second ends 610, 612. The first end 610 preferably has a larger radius near the joint stabilizer 620, and smaller radius at the second end near the retainer. The elastic element 606 provides traction to the thumb when the device is in use, and the elastic element 606 also allows for rotating the retainer during donning, which is important for the retainer.

The elastic element may comprise a variety of configurations beyond the spiral configuration depicted in the drawings. For example, the elastic element may be a "wave" spring that comprises a plurality of spring elements stacked on top of each other and forms a generally mesh appearance. Such a variation is useful in that it is generally cylindrical and may allow for the addition or removal of springs to modify the spring force and length of the elastic element. Another example is a ribbon or helical shaped spring that has a wider height, and may cover more of the thumb. The ribbon or helical shaped spring may have multiple helixes connected to one another. Yet another example may be a Belleville type spring comprising a plurality of washer disks stacked upon one another. Yet another example is a ribbon shaped loop spring whereby the spring of the elastic element comprises multiple loops formed from ribbons of springs placed between one another. Yet another example are magnetic springs whereby the at least two evenly loaded magnetic rings repel one another and therefore may provide the same effect as a spring. Yet another example is a helical or coil spring.

Referring to FIG. 33A, the retainer 630 secures on the interphalangeal (IP) joint of the thumb. The opening 632 of the retainer is preferably generally elliptical in shape bordered by wedge portions 634, 636 projecting from an inner periphery 638 of the retainer 630. Thus, by slipping the retainer 630 onto the thumb, past the IP joint, and then rotating it 90°, a narrower axis of the elliptical opening 632 engages with the IP joint to provide traction to the thumb.

FIGS. 33B and 33C offer another embodiment of a retainer. In this embodiment, the retainer 641 includes a base component 643 and an upper flange 645. The base component 643 defines a cylindrical portion 649 for receiving an elastic element which can abut against the upper flange 645. The upper flange 645 defines at least one handle 647 enabling rotation of the retainer 641 about an elastic element. The retainer 641 includes first and second wedge portions 651, 653 for securing against a thumb and prevent movement of the retainer 641 relative to the thumb once the elastic element is engaged.

Figure 33D:
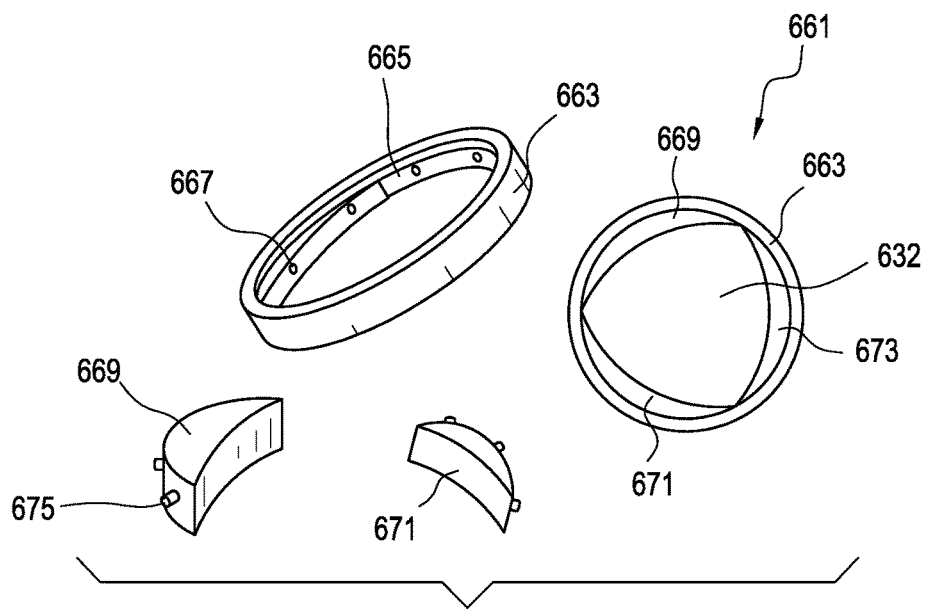
FIG. 33D is a perspective schematic view of another variation of a retainer.

FIG. 33D illustrates another retainer embodiment, wherein the retainer 661 defines a ring 663 having an inner surface 665 forming a plurality of apertures 667. Various wedges 669, 671, 673 are adapted to be placed against the inner surface 665 and have protrusions 675 arranged for insertion into the apertures 667 for securing against the inner surface 665. This arrangement enables the user to select among different wedge sizes according to the anatomy of the user, and therefore may provide a more custom fit.

Figure 33E:
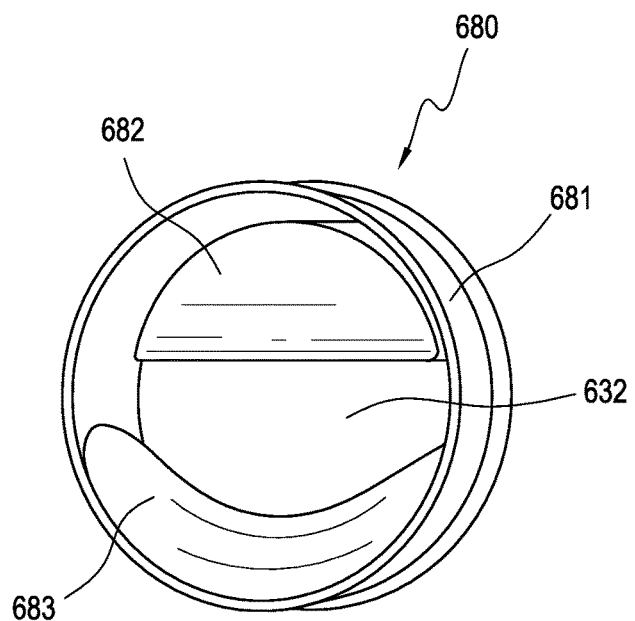
FIG. 33E is a plan view of another variation of a retainer.

FIG. 33E is another retainer embodiment wherein the retainer 680 has at least a ring 681, and first and second wedges 682, 683. The first wedge 682 may be pivotally connected to the ring 681 along its ends so the first wedge 682 acts as a flap against a thumb inserted into the ring. The second wedge 683 may likewise be pivotally connected, or alternatively may be stationary in the ring.

The wedges may be formed from rigid, semi-rigid or compressible materials. For example, the wedges may be formed from silicone that is adhered against the inner surface of the rings. The silicone may be sufficiently firm to prohibit movement of the retainer on the thumb, yet supple enough to enable gentle application or rotation of the retainer when the retainer is being placed or removed from the thumb.

According to a method, the retainer is in an open configuration so a tip of the thumb is inserted between at least two wedges of the retainer, with the wedges sufficiently spaced to permit the thumb tip to slide past them without significant resistance. The retainer may be rotatable relative to the elastic element for permitting the retainer to be in open and closed configurations. The retainer, as it may be biased by the elastic element, may then be pulled toward and past the thumb knuckle, and rotated relative to the thumb and the elastic element so the wedges are essentially turned in a generally perpendicular direction relative to the direction they were in when slipped over the tip of the thumb to place the retainer in a closed configuration. The wedges are sufficiently rigid, semi-rigid or compressible to maintain the retainer in place below and wedged (at the least the top portion of the wedges) against the knuckle between thumb saddle or web and relative to the thumb tip despite biasing by the elastic element. When it is desired to remove the retainer, the retainer may be rotated so it no longer wedges against the knuckle and is essentially in the open configuration for slipping past the knuckle and thumb tip.

Variations of retainers are provided to customize the size of the retainer. One variation includes a metal ring, such as one made from aluminum, that is overmolded with a soft material, such as silicone, that may likewise have portions formed into wedges. The metal ring may be cold formable to customize the shape to the user's thumb whereas the wedges and soft material accommodate the adjustment of ring size. In another variation, the retainer includes a ring that can be adjusted by pulling apart or pushing together a slot in the ring to adjust the diameter of the ring. In yet another variation, the retainer includes an outer ring having an oval configuration and an inner ring located within the outer ring. The inner ring can be rotated inside the outer ring to adjust the inner shape, with the inner ring having wedges as discussed above. In yet another embodiment, an outer ring has a threaded surface under an angle and the inner ring can be rotated inside the outer ring to adjust the size.

Referring to a preferred embodiment in FIGS. 34A and 34B, a hand support 900 comprises a base component 902 including a dorsal portion 910 and a palmar portion 904 arranged for securing about a hand or wrist or the base of the thumb, a strap 903 extending from the palmar portion 904 and adapted to wrap the hand or wrist and secure to the dorsal portion 910, a counterforce device comprising for example an elastic element 906 extending from the palmar portion 904 of the base component 902, and an anchor element comprising for example a retainer 908 securing to a second end 912 of the elastic element 906 and configured to secure along a thumb preferably below a thumb knuckle K. The elastic element 906 is arranged to bias between the retainer 908, which snugly secures to the thumb without movement as a result of biasing of the elastic element 906, and the base component 902. The hand support 900 may also be configured with a joint stabilizer 917 having similar components to the joint stabilizer 620 described in the earlier embodiments of FIGS. 29-32.

The elastic element 906 is generally spiral in configuration between first and second ends 911, 912. The first end 911 preferably has a larger radius near the base component 902 and a smaller radius near the retainer 908. As shown in FIG. 34B, the first end 911 is configured for attachment in a channel 920 provided in the palmar portion 904 of the base component 902. The elastic element 906 may be rotated into the channel 920 in order to increase or decrease the height of the elastic element above the base component 902 and for facilitating donning of the retainer 908 over the thumb. The support and channel may be arranged so the user or clinician can vary the degree by which the elastic element is inserted into the channel for adjusting a desired height or spring force of the elastic element. Alternatively, the elastic element 906 may be configured according to any of the configurations explained with respect to FIG. 31, for example, the elastic element 906 may comprise a helical or coil spring.

Figure 35:
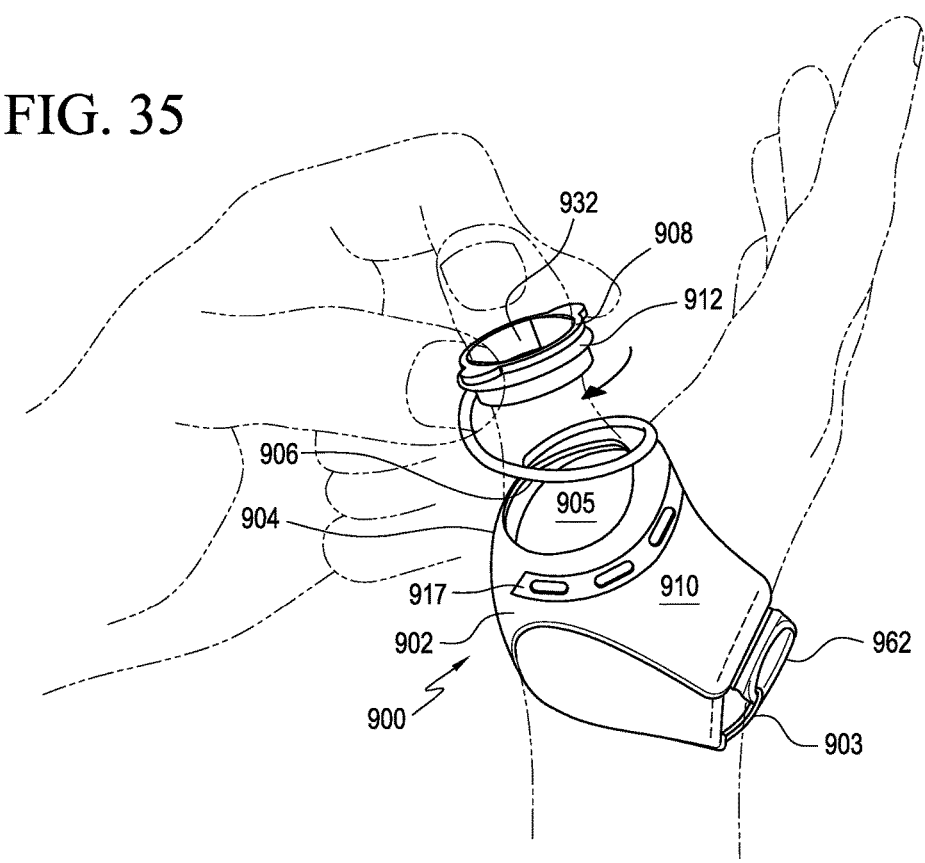
FIG. 35 is a perspective schematic view of the embodiment of FIG. 34A with adjustment of the retainer on a thumb.

The retainer 908 is configured for secure attachment to the thumb by rotation, similar to the retainer embodiment of FIG. 33A, but may comprise any number of shapes or elements for securely fastening to the thumb of the user and the elastic element 906. For example, the retainer 908 may be a ring having an opening 932 and may include a grip for a thumb including a wedge or a pair of wedges. As shown in FIG. 35, the retainer may be donned by rotating the retainer to a wide configuration for fitting to the thumb followed by rotating to a narrow configuration for securing to the thumb, preferably below the knuckle K of the thumb.

Dorsal and palmar portions 910, 904 of the base component 902 define an opening 905 adapted for insertion of a thumb, and extend across the dorsal and palmar portions, respectively, of the hand of the user. The portions 910, 904 extend and connect about the base of the thumb, both at or near the CMC joint and the thumb web, for creating a tight fit over the thumb. The base component 902 is preferably formed from a material or materials which are resilient enough to retain their shape during use but may be adjustable when fitted to a patient. The base component 902 may be thinner or more malleable as the distance from the opening 905 increases.

The dorsal portion 910 may terminate with a buckle 962 or other attachment means for securing the strap 903 and a fastener 960, such as hook and loop, latches, or interlocking components, for securing to the buckle 962 or similar elements and tightening around the wrist of the user.

Figure 36:
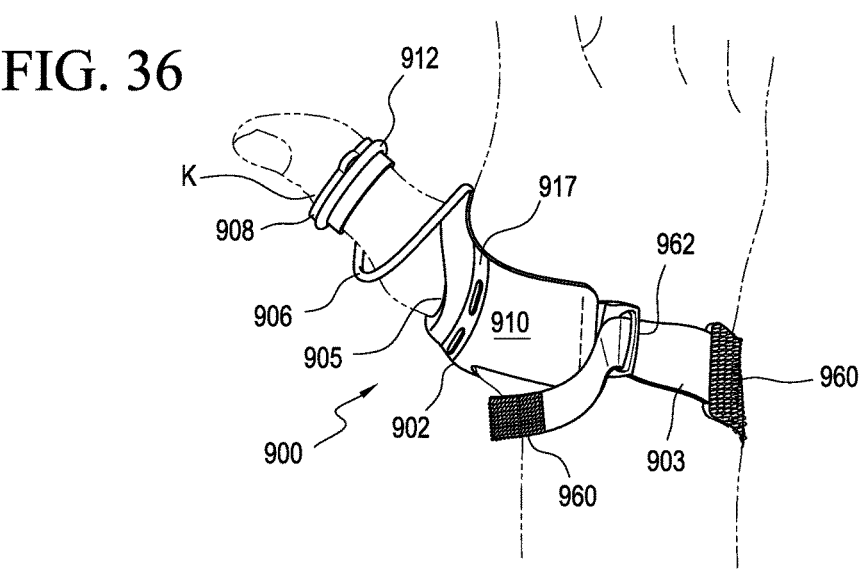
FIG. 36 is a perspective schematic view of the embodiment of FIG. 34A with adjustment about the wrist.

FIG. 36 exemplifies how the strap 903 tightens around the hand or wrist of a user for secure attachment of the hand support 900. A first end of the strap 903 is arranged for pulling away from the buckle 962 on the dorsal portion 910 and is selectively and lockingly placed over a portion of the strap. The strap 903 may be elastic or inelastic. In the event the strap 903 is elastic, by pulling the thumb away from the palm with an elastic closure, the support promotes correct anatomical position of the thumb. It is a known undesirable effect of CMC OA that a patient's hand deforms (the thumb goes into the palm).

Figure 37:
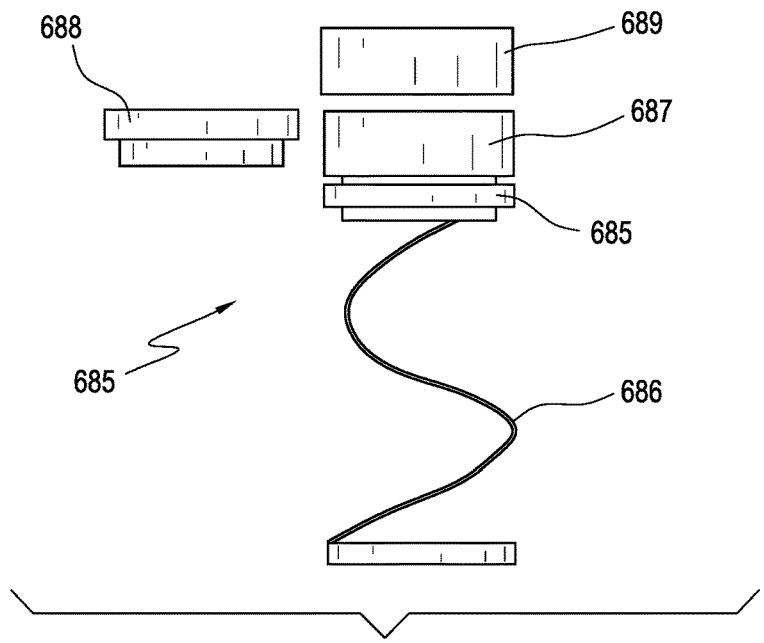
FIG. 37 is an elevational schematic view of a top spacer for a retainer in foregoing embodiments.

FIG. 37 shows an embodiment including a set 685 of different retainers and a spacer for fitting different thumb lengths. In the embodiment, at least two different retainers 687, 688 are provided, each having a different height for usage on different thumb lengths. A spacer 689 is provided that can engage the retainer and may include corresponding wedges for extending the length of the combination of the retainer 687 and elastic element 686. The set of retainers and spacer may be provided as a kit where the clinician can fit the support to the user's thumb length and the height of the spacers may be chosen to pretension the elastic element for the desired spring force.

Figure 38:
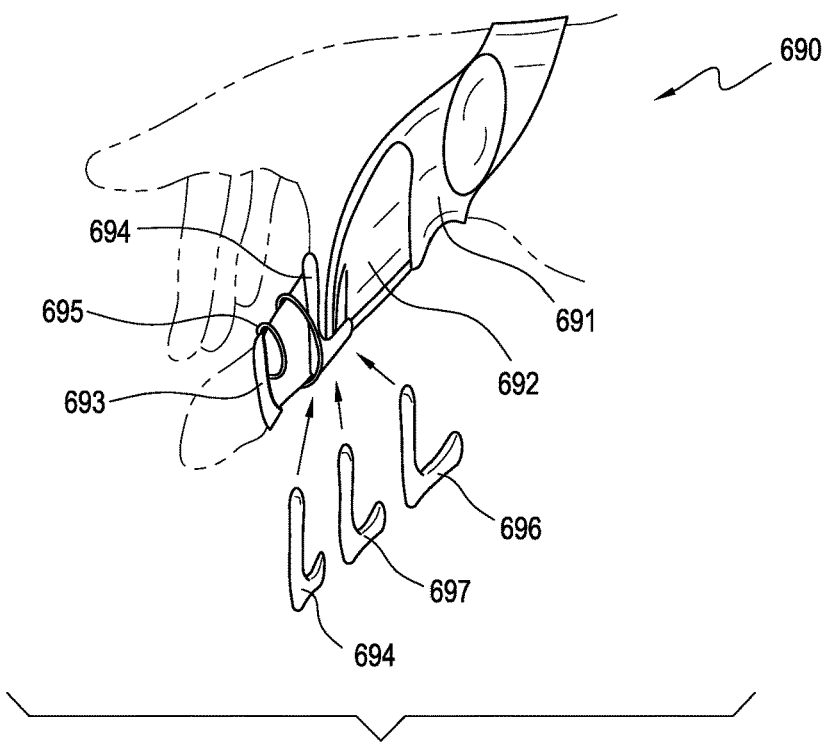
FIG. 38 is a perspective schematic view of a base spacer for a retainer in the foregoing embodiments.

FIG. 38 depicts a hand support 690 having a base component 691 and a joint stabilizer 692. A thumb retainer 693 is spaced from the joint stabilizer 692 by a plurality of spacers 694, 696, 697 and an elastic element 695. The spacers can be mounted on the elastic element, and may slide into the joint stabilizer to determine the length of the elastic element. The spacers may be provided to supplement the elastic element by increasing space between the joint stabilizer and the retainer, or may be used to increase the spring force by reducing the height of the elastic element. For example, a plurality of spacers 694, 696, 697 are provided with different heights, and a longer height may be used to compress the elastic element between the retainer and the spacer.

Figure 39A:
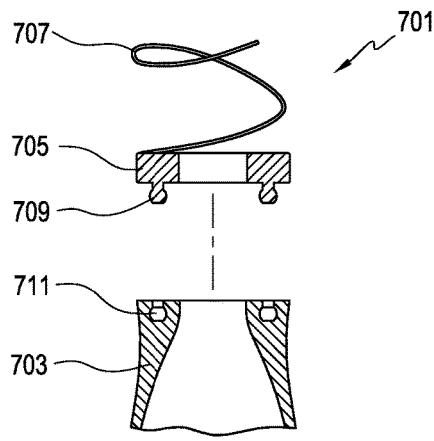
FIG. 39A is an elevational schematic view of showing a snap connection for an elastic element in foregoing elements.
Figure 39B:
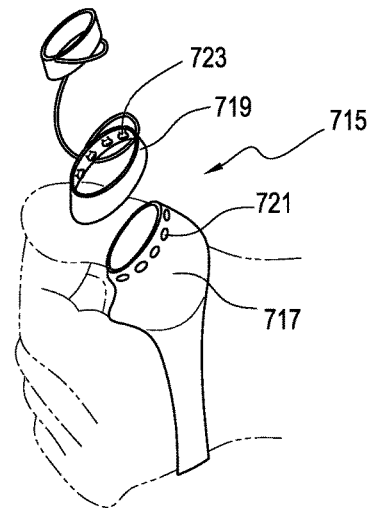
FIG. 39B is a perspective schematic view of the snap connection in FIG. 39A.

FIG. 39A shows an embodiment 701 wherein a snap connection is provided for the elastic element 707. A ring 705 is provided with snap elements 709 that are lockingly received by grooves 711 formed by a joint stabilizer 703. FIG. 39B depicts another embodiment 715 of a removable elongate element. The joint stabilizer 717 has a plurality of slots 721 formed about a top portion for receiving a plurality of pins 723 formed by a ring 719 adapted to carry the elongate element. These embodiments provide the clinician the ability to remove the elongate element should it not be required for use, and install the elongate element when it is needed.

Figure 40A:
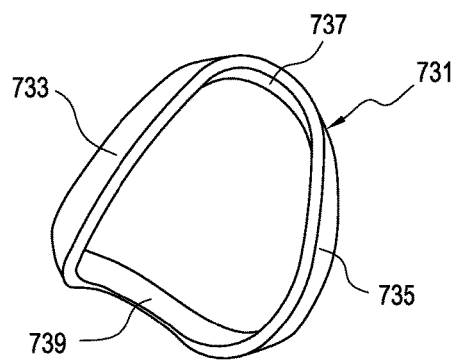
FIG. 40A is a perspective view of a saddle element for an alternate embodiment.
Figure 40B:
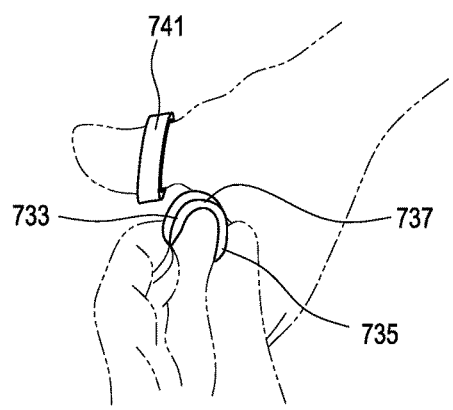
FIG. 40B is a perspective schematic view of the saddle element attached to a hand.
Figure 40C:
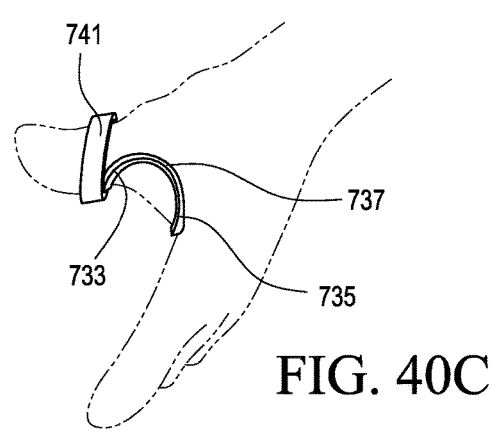
FIG. 40C is a perspective schematic view of the saddle element of FIG. 40A released on a hand.

FIGS. 40A-40C illustrate a thumb traction embodiment relying on a saddle element 731 to bias the retainer on the thumb. The saddle element 731 defines a spring having first and second arms 733, 735 connected to first and second hinges 737, 739. A retainer 741, such as those discussed above, is inserted over the thumb, and the first and second arms 733, 735 of the saddle element 731 are compressed between the thumb saddle of the user by the hinges 737, 739 and connected to the retainer. The saddle element 731 rests over the thumb saddle of the user, which the hinges 737, 739 extending over opposed sides of the thumb saddle. The saddle element delivers force on a first side of the thumb retainer and offsets the ring to pinch the thumb.

Figure 41:
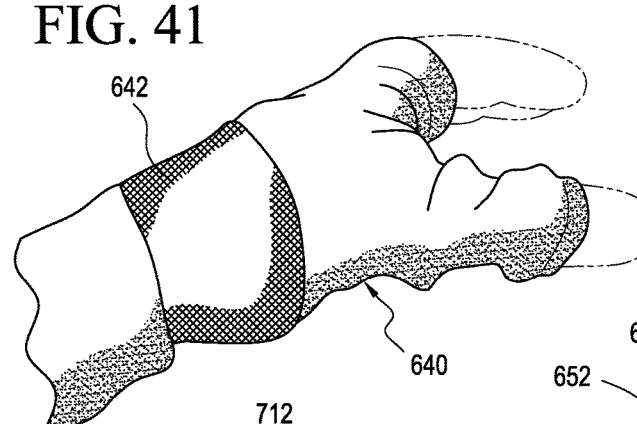
FIG. 41 is a perspective view of a sleeve covering the thumb support of FIG. 29A.

FIG. 41 exemplifies how a sleeve 640 can be provided over the embodiment of FIGS. 29A and 29B, and a strap 642 may be provided over the sleeve 640 to aid in retaining the hand support on the hand of a user. The sleeve may be formed from a textile or otherwise breathable and flexible material to enable articulation of the hand and the components of the hand support.

Figure 42:
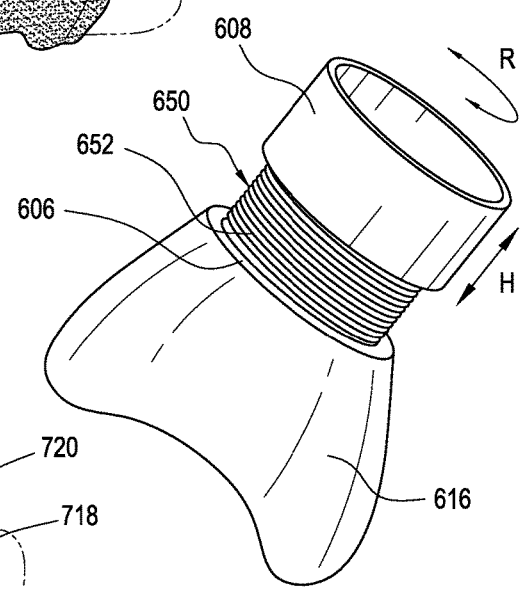
FIG. 42 is a schematic view of a variation of the thumb support of FIG. 29A.

FIG. 42 shows an alternative embodiment of the hand support 650 of FIGS. 29A and 29B. According to this embodiment, a sleeve 652 preferably having a tubular shape extends from the reinforcement component 616 such that the retainer 608 can adjust in height H relative to the reinforcement component 616 to increase or decrease tension in the elastic element 606. The retainer 608 may be rotatable in directions R to increase or decrease the height of the elastic element 606. The retainer 608 may be screwable or ratcheting relative to the sleeve 652 by known methods. The sleeve 652 may be flexible or semi-rigid sufficiently to enable articulation of the elastic element 606 to move relative thereto.

Figure 43:
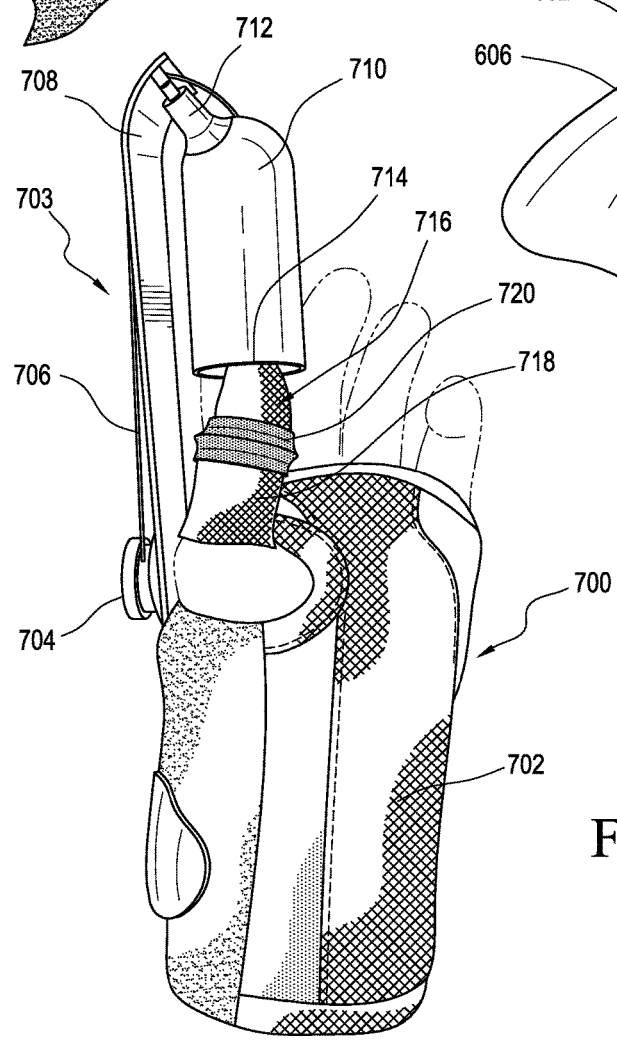
FIG. 43 is a perspective view of another thumb traction device.

FIG. 43 illustrates a hand support 700 having a traction system 703 relying on a seal element 716 for securing a thumb arrest 710 thereto. The hand support includes a base component 702 for mounting on the wrist, hand or both. In a preferred embodiment, the base component 702 is a hand wrap.

The traction system 703 is secured to the base component 702. A tensioning device 704 secures to a bar 708 having a first end mounted to the base component 702. The tensioning device 704 includes an elongate element 706 routed about the bar 708 and tethered at a second end of the bar 708. A coupler 712 connects the second end of the bar 708 to a second end of the thumb arrest 710, to thereby cantilever the bar, particularly by tensioning the elongate element 706 and the bar 708 may serve as a spring for effectively pulling the thumb which is secured therewith by insertion of the thumb with the seal element 716 located within the thumb arrest 710.

The thumb arrest 710 defines an opening 714 at a first end through which the thumb is inserted with the seal element 716. According to a preferred embodiment, the seal element 716 defines a sleeve 718 arranged for being disposed over the thumb. A seal 720 radially extends from the sleeve 718 for engaging an inner surface (not shown) of the thumb arrest 710.

A vacuum is effectively formed within the thumb arrest 710 to maintain a connection between the thumb arrest 710 and the thumb in a gentle manner that does not restrict blood flow. From the connection, an increase in the CMC joint gap in the thumb is enabled by gradual tensioning of the tensioning device 704 and flexure of the bar 708.

FIG. 44 shows different possibilities of the seal element useable with the hand support 700. For example, in a first seal element 750, the sleeve 752 is constructed from a flexible material, such as a textile or polymeric material, arranged for frictionally engaging the thumb. The seal element 750 includes first and second circumferential seals 754, 756 that are arranged to frictionally engage an inner surface of the thumb arrest. A second seal element 758 includes a sleeve 760 and a single circumferential seal 762. Of course, the first and second seal elements 750, 758 may be adapted to include any number of seal elements and are not limited to the embodiments shown herein.

FIG. 44 also shows a third seal element 764 having a sleeve 766 and a seal element 768 having any of the seals taught in U.S. patent application publication No. 2015/0142131, published on May 21, 2015, and incorporated herein by reference. The seal element 768 may be adjustably secured to the sleeve 766 so placement of the seal may be selected by the user or the seal may be permanently secured to the sleeve 766 at the desired location.

FIG. 45 depicts another hand support 800. In this embodiment, the hand support 800 includes a base component 802 adapted for securing about the base of the thumb, and a movable component 804 adapted for securing about and proximate to a knuckle of the thumb. The movable component 804 may include a seal or band 808 located at a first end of the movable component 804 for circumferentially engaging the thumb. The seal or band may have a construction of any of the other seals described herein. A tensioning device 806 is provided which includes an elongate element 807 extending through a plurality of guides 810 located at end portions of the base component 802 and movable component 804. The end portions of the base component 802 comprise a first set of fingers 814 that alternate and correspond to a second set of openings 820 formed between a second set of fingers 816 of the movable component 804. The first set of fingers 814 define a first set of openings 818 into which the second set of openings 820 extend.

In a closed or contracted configuration in FIG. 46, the first and second sets of fingers 814, 816 generally extend fully into the first and second sets of openings 818, 820, respectively. Upon adjustment of the tensioning device 806, as depicted in FIG. 39, the elongate element 807 slides through the guides 810 to extend the movable component 804 relative to the base component 802. As shown, the end portions of the first and second sets of fingers 814, 816 are generally drawn toward one another, while the first and second sets of openings 818, 820 open significantly. The extension of the movable component 804 relative to the base component 802 can occur slowly and incrementally as a result of adjustment of the tensioning device 806 to slowly and gently open the CMC joint.

While the foregoing embodiments have been described and shown, alternatives and modifications of these embodiments, such as those suggested by others may be made to fall within the scope of the invention. While the hand support has been described in combination with or without traction means, it will be understood that the principles described may be extended to other types of orthopedic and prosthetic devices.

Reference characters are provided in the claims for explanatory purposes only and are not intended to limit the scope of the claims or restrict each claim limitation to the specific element shown in the drawings and identified by the reference character.

The invention claimed is:

1. A hand support, comprising:
a base component arranged for securing to at least a portion of a hand, and forming a base opening adapted for insertion of a thumb;
an anchor element adjustably connected to the base component and arranged for grasping the thumb;
a counterforce device defined by a helical spring having a first end connecting to the base component and surrounding the base opening and extending distally therefrom, and a second end holding the anchor element and distally located relative to the base component, the helical spring arranged to generate a counterforce in combination with or against the base component and the anchor element, the helical spring spanning a distance between the base component and the anchor element, and arranged for encircling the thumb, the anchor element being biased by and rotatable relative to the helical spring, the helical spring being compressible in height relative to and from the base component.

2. The hand support of claim 1, further comprising a joint stabilizer extending about the base component, the joint stabilizer having greater rigidity than the base component.

3. The hand support of claim 2, wherein the joint stabilizer has a base portion upon which the counterforce device secures, the base portion having greater rigidity than the first and second ends.

4. The hand support of claim 2, wherein the joint stabilizer is constructed from a malleable material.

5. The hand support of claim 2, wherein the joint stabilizer generally defines a J-shape, with a first end having a taper for mounting about a dorsal aspect of a hand, and a second end adapted for wrapping about at least part of a palmar aspect of the hand, the first and second ends extending from a base portion extending about a base of the thumb between the dorsal and palmar aspects of the hand.

6. The hand support of claim 1, wherein the anchor element is annular in shape and defines a ring opening, the anchor element is rotatably secured to the second end of the counterforce device.

7. The hand support of claim 6, wherein the anchor element includes at least one wedge portion located about and extending into the ring opening, the at least one wedge portion arranged to suspend the anchor element on the thumb and counteract forces exerted by the counterforce device.

8. The hand support of claim 7, wherein the at least one wedge portion includes first and second wedges protruding from an inner surface of the anchor element and into the ring opening.

9. The hand support of claim 1, wherein the base component defines a dorsal portion and a palmar portion arranged for securing about a hand or wrist, and a strap extending from the palmar portion and adapted to wrap about the hand or wrist.

10. The hand support of claim 9, wherein a first end of the strap is arranged for pulling away from a buckle on the dorsal portion, and selectively and lockingly placed over a portion of the strap.

11. A method for securing a hand support over a hand, the method comprising the steps of:
   securing a base component about a thumb of a user, the base component having a base opening adapted for insertion of the thumb;
   extending a counterforce device from the base component, the counterforce device being a helical spring having a first end connecting to the base component and surrounding the base opening to extend distally therefrom, the helical spring being compressible in height and elastic relative to and toward the base opening;
   adjusting an anchor element on a second end of the counterforce device located at a distal end of the helical spring;
   biasing the counterforce device between the anchor element and the counterforce device due to the elasticity and compressibility of the helical spring.

12. The method of claim 11, further comprising the step of:
   rotating the anchor element on the counterforce device between an open configuration and a closed configuration, the anchor element forming a ring opening having at least one wedge portion located on an interior side thereof and extending into the ring opening, the anchor element placed in first and second positions corresponding to the open and closed configurations, respectively.

13. The method of claim 12, wherein the anchor element is annular and defines an opening into which the at least one wedge portion extends, the open configuration corresponding to a tip of the thumb and the closed configuration corresponding to engagement of a thumb knuckle.

14. The method of claim 11, wherein the base component defines a dorsal portion and a palmar portion arranged for securing about a hand or wrist, and a strap extending from the palmar portion and adapted to wrap about the hand or wrist;
   wherein the method further comprises the step of pulling away a first end of the strap from a buckle on the dorsal portion and securing the first end of the strap over a portion of the strap.

15. The method of claim 11, wherein the hand support further comprises a joint stabilizer connecting to the base component and being constructed from a malleable material;
   wherein the method further comprises the step of securing the joint stabilizer about a base portion of the thumb.

16. A hand support, comprising:
   a base component arranged for securing to at least a portion of a hand, the base component having a base opening;
   a joint stabilizer connecting to the base component and arranged for securing the joint stabilizer about a base portion of a thumb;
   an anchor element having an annular shape and adjustably connected to the joint stabilizer about the base opening, the anchor element having at least one wedge portion arranged for having an open configuration and a closed configuration for insertion of the thumb therethrough and locking against the thumb, respectively;
   a counterforce device formed as an elastic element having a first end secured to the joint stabilizer about the base opening, and a second end connecting to the anchor element, the elastic element arranged for encircling about the thumb and biasing between the joint stabilizer and/or the anchor element.

* * * * *